(12) United States Patent
Honda et al.

(10) Patent No.: US 8,449,455 B2
(45) Date of Patent: May 28, 2013

(54) MEDICAL SYSTEM FOR A PLURALITY OF OPERATORS TO PERFORM AN OPERATION OF ONE MEDICAL INSTRUMENT IN COLLABORATION

(75) Inventors: Kazuki Honda, Hachioji (JP); Wataru Matsuura, Sagamihara (JP); Yasuhito Kura, Hachioji (JP); Yuji Sakamoto, Kunitachi (JP)

(73) Assignee: Olympus Medical Systems Corp., Tokyo (JP)

( * ) Notice: Subject to any disclaimer, the term of this patent is extended or adjusted under 35 U.S.C. 154(b) by 204 days.

(21) Appl. No.: 12/899,697

(22) Filed: Oct. 7, 2010

(65) Prior Publication Data

US 2011/0208000 A1  Aug. 25, 2011

Related U.S. Application Data

(63) Continuation of application No. PCT/JP2010/060288, filed on Jun. 17, 2010.

(30) Foreign Application Priority Data

Jun. 23, 2009 (JP) ................................. 2009-148814

(51) Int. Cl.
*A61B 1/00* (2006.01)
*G05B 23/02* (2006.01)

(52) U.S. Cl.
USPC ............................ 600/118; 600/106; 340/3.1

(58) Field of Classification Search
USPC . 600/103, 106, 117, 118; 700/9; 340/3.1–3.3; 606/130
See application file for complete search history.

(56) References Cited

U.S. PATENT DOCUMENTS 5,622,528 A * 4/1997 Hamano et al. ............... 600/118
6,659,939 B2 * 12/2003 Moll et al. ..................... 600/102
(Continued)

FOREIGN PATENT DOCUMENTS

EP  1 902 661 A1  3/2008
EP  2 064 984 A2  6/2009
(Continued)

OTHER PUBLICATIONS

JP Office Action of corresponding JP Application No. JP 2010-538677 dated Jan. 5, 2011 with English language translation.
(Continued)

*Primary Examiner* — John P Leubecker
(74) *Attorney, Agent, or Firm* — Scully, Scott, Murphy & Presser, P.C.

(57) ABSTRACT

A medical system includes: a first operation apparatus used when a first doctor operates a medical instrument; a second operation apparatus that outputs a control instruction signal for controlling a motion of the medical instrument, and is operated by a second doctor; at least one medical action information detection section that detects medical action information based on the motion of the medical instrument when the first doctor operates the medical instrument using the first operation apparatus; a storage apparatus that stores reference information set by the second doctor according to the first doctor for comparing with the medical action information detected by the medical action information detection section; a switching signal generation apparatus that is connected to the second operation apparatus, and switches an output destination of the control instruction signal based on the medical action information detected by the medical action information detection section and the reference information stored in the storage apparatus; and a medical instrument control apparatus that controls the medical instrument according to the control instruction signal of the second operation apparatus outputted from the switching signal generation apparatus.

8 Claims, 12 Drawing Sheets

U.S. PATENT DOCUMENTS

| | | | |
|---|---|---|---|
| 6,726,675 B1 * | 4/2004 | Beyar | 604/510 |
| 6,799,088 B2 * | 9/2004 | Wang et al. | 700/258 |
| 7,171,286 B2 * | 1/2007 | Wang et al. | 700/248 |
| 7,386,730 B2 * | 6/2008 | Uchikubo | 713/182 |
| 7,485,115 B2 * | 2/2009 | Nakamura | 606/1 |
| 7,979,157 B2 * | 7/2011 | Anvari | 700/245 |
| 2002/0147384 A1 * | 10/2002 | Uchikubo | 600/109 |
| 2006/0149418 A1 | 7/2006 | Anvari | |
| 2006/0178559 A1 | 8/2006 | Kumar et al. | |
| 2007/0083480 A1 | 4/2007 | Ozaki et al. | |
| 2008/0039685 A1 * | 2/2008 | Komiya et al. | 600/106 |
| 2009/0099576 A1 * | 4/2009 | Wang et al. | 606/130 |
| 2009/0143642 A1 | 6/2009 | Takahashi et al. | |

FOREIGN PATENT DOCUMENTS

| | | |
|---|---|---|
| JP | 61-76129 | 4/1986 |
| JP | 05-211993 | 8/1993 |
| JP | 06-277176 | 10/1994 |
| JP | 2000-014635 | 1/2000 |
| JP | 2000-271147 | 10/2000 |
| JP | 2002-065575 | 3/2002 |
| JP | 2005-110846 | 4/2005 |
| JP | 2005-111080 | 4/2005 |
| JP | 2006-325838 | 12/2006 |
| JP | 2007-075520 | 3/2007 |
| JP | 2009-131374 | 6/2009 |
| WO | WO 2007/018289 A1 | 2/2007 |

OTHER PUBLICATIONS

JP Office Action of corresponding JP Application No. JP 2010-538677 dated Nov. 16, 2010 with English language translation.
European Search Report issued in corresponding European Patent Application No. EP 10 79 2015.9 dated Feb. 6, 2012.

* cited by examiner

| CONTRACTION FORCE < THRESHOLD? | INSERTION PORTION MOVEMENT AMOUNT = DISTAL END PORTION MOVEMENT AMOUNT | GRASPING FORCE < THRESHOLD? | PROCEDURE SITUATION |
|---|---|---|---|
| 1 | 1 | 1 | 1 |
| 1 | 1 | 2 | 1 |
| 1 | 2 | 1 | 1 |
| 1 | 2 | 2 | 2 |
| 2 | 1 | 1 | 1 |
| 2 | 1 | 2 | 2 |
| 2 | 2 | 1 | 2 |
| 2 | 2 | 2 | 2 |

| HEART RATE <THRESHOLD? | BENDING OPERATION ANGLE = BENDING PORTION BENDING ANGLE? | FREQUENCY OF BENDING OPERATION <THRESHOLD? | PROCEDURE SITUATION |
|---|---|---|---|
| 1 | 1 | 1 | 0 |
| 1 | 1 | 2 | 1 |
| 1 | 2 | 1 | 1 |
| 1 | 2 | 2 | 2 |
| 2 | 1 | 1 | 1 |
| 2 | 1 | 2 | 2 |
| 2 | 2 | 1 | 2 |
| 2 | 2 | 2 | 2 |

MEDICAL SYSTEM FOR A PLURALITY OF OPERATORS TO PERFORM AN OPERATION OF ONE MEDICAL INSTRUMENT IN COLLABORATION

CROSS REFERENCE TO RELATED APPLICATION

This application is a continuation application of PCT/JP2010/060288 filed on Jun. 17, 2010 and claims benefit of Japanese Application No. 2009-148814 filed in Japan on Jun. 23, 2009, the entire contents of which are incorporated herein by this reference.

BACKGROUND OF THE INVENTION

1. Field of the Invention

The present invention relates to a medical system for a plurality of operators to perform an operation of one medical instrument in collaboration.

2. Description of the Related Art

In recent years, endoscopes have been widely used in a medical field. An endoscope includes an elongated insertion portion, and can perform observation by inserting the insertion portion into a body. Also, a treatment instrument may be inserted into the body through a treatment instrument channel provided in the insertion portion of the endoscope to perform various tests, therapies, or treatments.

A general endoscope is configured in such a way that a bending portion that can be vertically and laterally bent by an operator's hand operation is provided on a distal end side of an insertion portion. The bending portion can be bent in a desired direction by a pulling/slackening operation of a bending wire inserted through the insertion portion.

The bending wire is generally operated by a manual operation of a bending operation knob or a bending operation lever provided in an operation section connected to a proximal end of the insertion portion. In recent years, in order to reduce a load on an operator who operates a bending operation knob or the like, an electric bending endoscope apparatus has been proposed configured to perform a pulling/slackening operation of a bending wire using electric bending driving means such as an electric motor.

When an insertion portion of an endoscope is inserted into an intricate tube cavity, for example, a large intestine, an operator operates, for example, a bending knob to bend a bending portion, and twists the insertion portion to insert a distal end portion of the insertion portion toward an observation target area. However, short-time and smooth insertion of the insertion portion to a deep target area in the large intestine without giving pain to a patient requires skill. An inexperienced operator may lose track of an insertion direction and be slow to insert the insertion portion to the deep area, or may significantly deform a course of the intestine to give pain to the patient. Thus, in recent years, a medical system has been proposed that can easily insert an insertion portion to a target area of a tube cavity.

A recent medical system includes, for example, an electronic endoscope having a bending portion, a light source apparatus that supplies an illuminating light to the electronic endoscope, a camera controller having an image processing circuit for displaying an endoscopic image, and a monitor that displays the endoscopic image, and further includes, for example, a pneumoperitoneum apparatus, a high frequency cauterization apparatus, or the like as peripheral apparatuses.

In this medical system, under endoscopic observation, observation, therapies, treatments, or surgeries can be performed such as endoscopic therapies including endoscopic mucosal resection in which an injection solution is injected to a submucosa immediately below cancer cell in mucosa to release the mucosa and then only the mucosa containing the cancer cell is resected, or polypectomy in which a polyp is resected by a high frequency snare. Thus, doctors are demanded to acquire and improve an insertion technique, and also acquire endoscopic therapies and treatments and improve techniques thereof.

In such a medical system, an inexperienced doctor (hereinafter referred to as a lower doctor) acquires a technique under the supervision of a skilled doctor (hereinafter referred to as an upper doctor). Specifically, under endoscopic observation, the lower doctor together with the upper doctor observes an endoscopic image displayed on a monitor. Then, the lower doctor is verbally instructed or directly guided by the upper doctor, and thus can insert an insertion portion, for example, into a large intestine to reliably perform large intestine endoscopy.

For example, Japanese Patent Laid-Open No. 2000-271147 discloses a telesurgery system in which an upper doctor in a remote place can observe an endoscopic image via a communication line, and change the endoscopic image to a desired state by a hand operation to appropriately support a lower doctor in an operating room.

SUMMARY OF THE INVENTION

The present invention provides a medical system including: a first operation apparatus used when a first doctor operates a medical instrument; a second operation apparatus that outputs a control instruction signal for controlling a motion of the medical instrument, and is operated by a second doctor; at least one medical action information detection section that detects medical action information based on the motion of the medical instrument when the first doctor operates the medical instrument using the first operation apparatus; a storage apparatus that stores reference information set by the second doctor according to the first doctor for comparing with the medical action information detected by the medical action information detection section; a switching signal generation apparatus that is connected to the second operation apparatus, and switches an output destination of the control instruction signal based on the medical action information detected by the medical action information detection section and the reference information stored in the storage apparatus; and a medical instrument control apparatus that controls the medical instrument according to the control instruction signal of the second operation apparatus outputted from the switching signal generation apparatus.

BRIEF DESCRIPTION OF THE DRAWINGS

FIG. 1 is a diagram explaining a configuration of an endoscope system;

FIG. 2 is a diagram explaining an insertion portion grasping grip;

FIG. 3 is a diagram explaining a state of use of the insertion portion grasping grip;

FIG. 4 is a diagram explaining a guide tube and an insertion portion advancing/retracting apparatus that constitute an anus fitting tool;

FIG. 5 is a sectional view taken along the line V-V in FIG. 4;

FIG. 6 is a diagram explaining a relationship between determination results of a determination section and switching signals outputted from a control instruction section;

FIG. 7 is a diagram explaining an example of displaying detection values detected by medical action information detection sections on a screen of a detection monitor;

FIG. 8 is a flowchart explaining an exemplary collaborative operation of an endoscope system by two doctors;

FIG. 9 is a diagram explaining another configuration of an endoscope system;

FIG. 10 is a diagram explaining a bending angle detection apparatus;

FIG. 11 is a diagram explaining an upper doctor viewer;

FIG. 12 is a diagram explaining a relationship between determination results of a determination section and switching signals outputted from a control instruction section;

FIG. 13 is a diagram explaining a relationship between a switching section and an output section when a third switching signal is outputted from the control instruction section to a signal output switching section;

FIG. 14 is a diagram explaining a relationship between the switching section and the output section when a fourth switching signal is outputted from the control instruction section to the signal output switching section;

FIG. 15 is a diagram explaining a relationship between the switching section and the output section when a fifth switching signal is outputted from the control instruction section to the signal output switching section;

FIG. 16 is a flowchart explaining an exemplary collaborative operation of an endoscope system by two doctors;

FIG. 17 is a flowchart explaining an collaborative operation of an endoscope by two doctors in an insertion step; and FIG. 18 is a flowchart explaining a collaborative operation of the endoscope by two doctors in a treatment step.

DETAILED DESCRIPTION OF THE PREFERRED EMBODIMENTS

Now, embodiments of the present invention will be described with reference to the drawings.

A first embodiment of the present invention will be described with reference to FIGS. 1 to 8.

Figure 1:
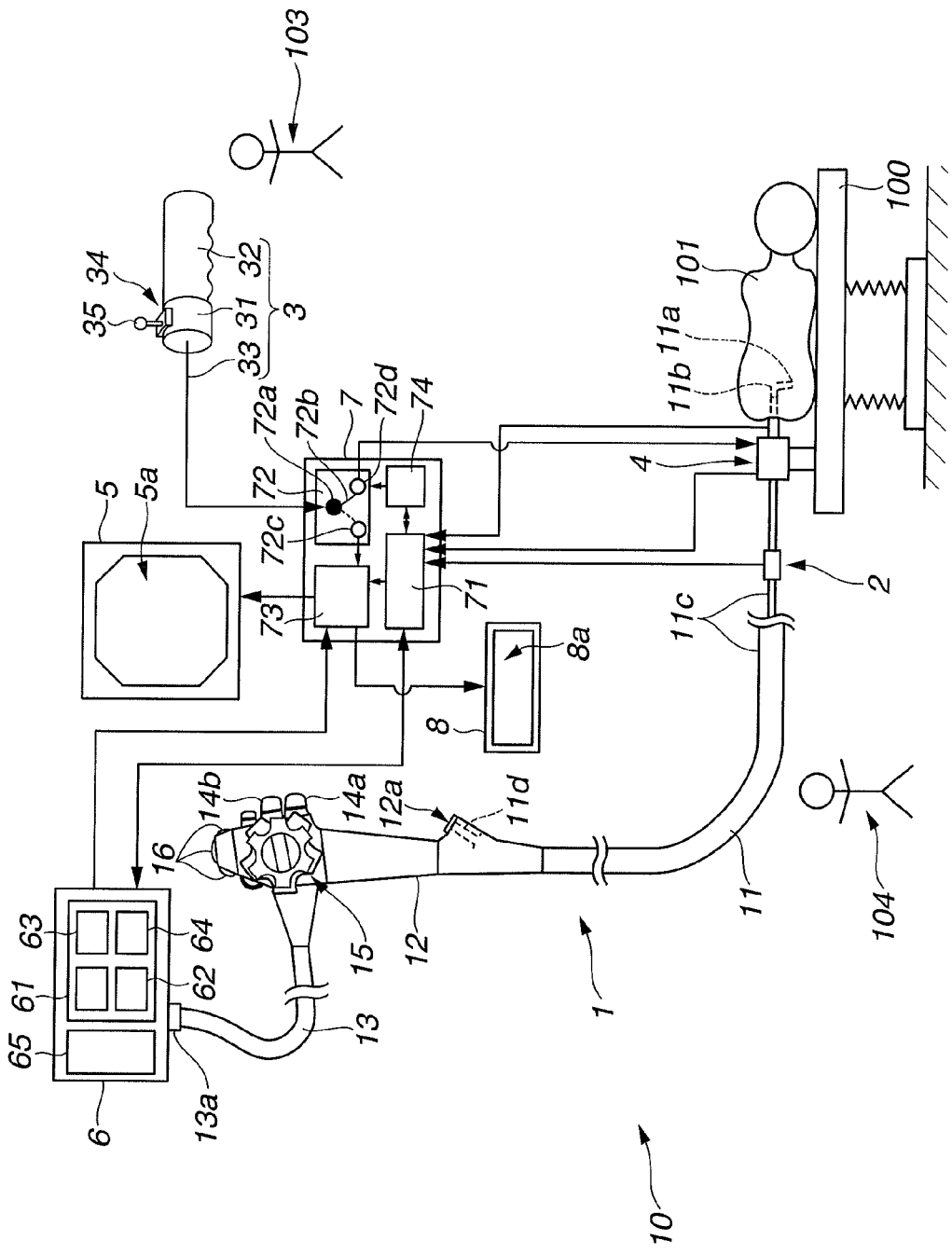
FIGS. 1 to 8 relate to a medical system according to a first embodiment of the present invention.

As shown in FIG. 1, a medical system 10 of this embodiment mainly includes an endoscope 1 as a medical instrument, a lower doctor insertion portion grasping grip (hereinafter simply referred to as an insertion portion grasping grip) 2 as a first operation apparatus, an upper doctor controller (hereinafter simply referred to as a controller) 3 as a second operation apparatus, an anus fitting tool 4, an endoscope monitor 5 and a detection value display monitor (hereinafter simply referred to as a detection monitor) 8 as display apparatuses, and an endoscope control apparatus 6 and a determination control apparatus 7 as control apparatuses. Reference numeral 100 denotes a bed, on which a patient 101 lies.

The endoscope 1 is a so-called electronic endoscope including an image pickup device such as a CCD. The endoscope 1 includes an insertion portion 11, an operation section 12, and a universal cord 13. The operation section 12 also serves as a grasping portion, and is provided at a proximal end side of the insertion portion 11. The universal cord 13 extends, for example, from a side portion of the operation section 12, and a connector 13a at a proximal end thereof is detachably connected to the endoscope control apparatus 6.

The insertion portion 11 includes a rigid distal end portion 11a, a bendable bending portion 11b, and a flexible tube portion 11c connected in order from a distal end side. The operation section 12 includes an air/water supply button 14a, a suction button 14b, a bending knob 15, various image switches 16, or the like. The air/water supply button 14a is a button for air/water supply. The suction button 14b is a button for suction. The bending knob 15 is used for bending the bending portion 11b. The bending portion 11b is bent by rotating the bending knob 15 clockwise or counterclockwise. The image switches 16 perform control to stop an endoscopic image picked up by an image pickup device provided in the distal end portion 11a, and displayed on a screen 5a as an information display section of the endoscope monitor 5.

The endoscope 1 includes a treatment instrument insertion channel 11d that provides communication between a treatment instrument leading port (not shown) formed in the distal end portion 11a, and a treatment instrument insertion port 12a in the operation section 12. The treatment instrument insertion channel 11d is an introduction path for introducing a treatment instrument into a body cavity. Biopsy forceps, a high frequency cauterization apparatus, or the like can be introduced into a body through the treatment instrument insertion channel 11d to perform tests, treatments, or the like.

Figure 2:
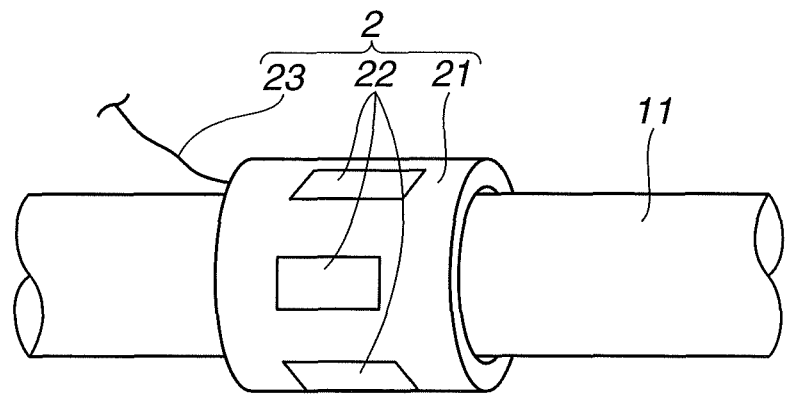

The insertion portion grasping grip 2 is one of medical action information detection sections. The insertion portion grasping grip 2 is used when a doctor (hereinafter referred to as a lower doctor) 104 who is inexperienced in, for example, large intestine endoscopy as a first doctor takes charge of a procedure. The insertion portion grasping grip 2 is a first operation apparatus, and as shown in FIG. 2, includes a grip body 21, a plurality of pressure sensors 22, and a signal wire 23. The signal wire 23 is extended from the grip body 21 and connected to the determination control apparatus 7 as shown in FIG. 1.

The grip body 21 is formed of an elastic member such as a silicone tube into a tubular shape. The grip body 21 is deformed with increasing grasping force, and restored to its original shape with decreasing grasping force. The grip body 21 is fitted to an outer circumferential side of the insertion portion 11.

Figure 3:
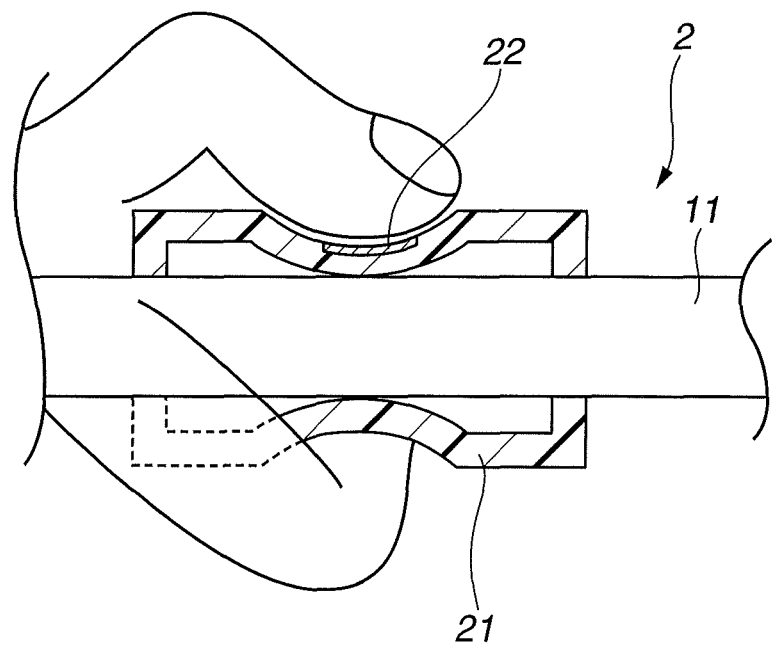

A plurality of pressure sensors 22 are arranged in a circumferential direction of an outer circumference of the grip body 21. The pressure sensor 22 is an operator pressure sensor, and an operation information detection section. The pressure sensor 22 detects an insertion portion grasping force of an operator as operation input information as medical action information. Specifically, the operator pressure sensor 22 detects a grasping force of the operator via the grip body 21 of the insertion portion grasping grip 2 when the operator grasps the insertion portion 11 as shown in FIG. 3. A detection value of the operator pressure sensor 22 is outputted via the signal wire 23 to the determination control apparatus 7.

The controller 3 is used by a skilled doctor (hereinafter referred to as an upper doctor) 103 as a second doctor, for example, when the upper doctor observes the procedure of the lower doctor 104. As shown in FIG. 1, the controller 3 is a second operation apparatus. The controller 3 is, for example, a substantially cylindrical shape, and includes a rigid main body 31, a grip portion 32 connected to a proximal end side of the main body 31, and a signal wire 33. The grip portion 32 is formed of, for example, an elastic member in view of a grasping property. The signal wire 33 is extended, for example, from the main body 31 and connected to the determination control apparatus 7.

The main body 31 includes a manual operation section 34 in a predetermined position. The manual operation section 34 has an operation lever 35 of a so-called joystick type that can be tilted. In this embodiment, the operation lever 35 is a home position return switch that can be tilted to a distal end side and a proximal end side of the main body 31 while being grasped by the operator. The operation lever 35 may be a home position return switch that can be tilted to right and left viewed from the operator while being grasped by the operator.

The manual operation section 34 is configured in such a way that a head of the operation lever 35 is tilted to the distal end side or the proximal end side to output a control instruction signal. When the head of the operation lever 35 is tilted to the distal end side, the controller 3 outputs a control instruction signal having a control signal and an operation instruction for advancing the insertion portion 11. Meanwhile, when the head of the operation lever 35 is tilted to the proximal end side, the controller 3 outputs a control instruction signal having a control signal and an operation instruction for retracting the insertion portion 11.

In this embodiment, advancing/retracting speeds of the insertion portion 11 are changed depending on tilt angles of the operation lever 35. Specifically, with a small tilt angle of the operation lever 35, the controller 3 outputs a control instruction signal for reducing the advancing speed or the retracting speed. Then, the controller 3 outputs a control instruction signal for setting a speed to a predetermined insertion speed with increasing tilt angle of the operation lever 35.

Figure 4:
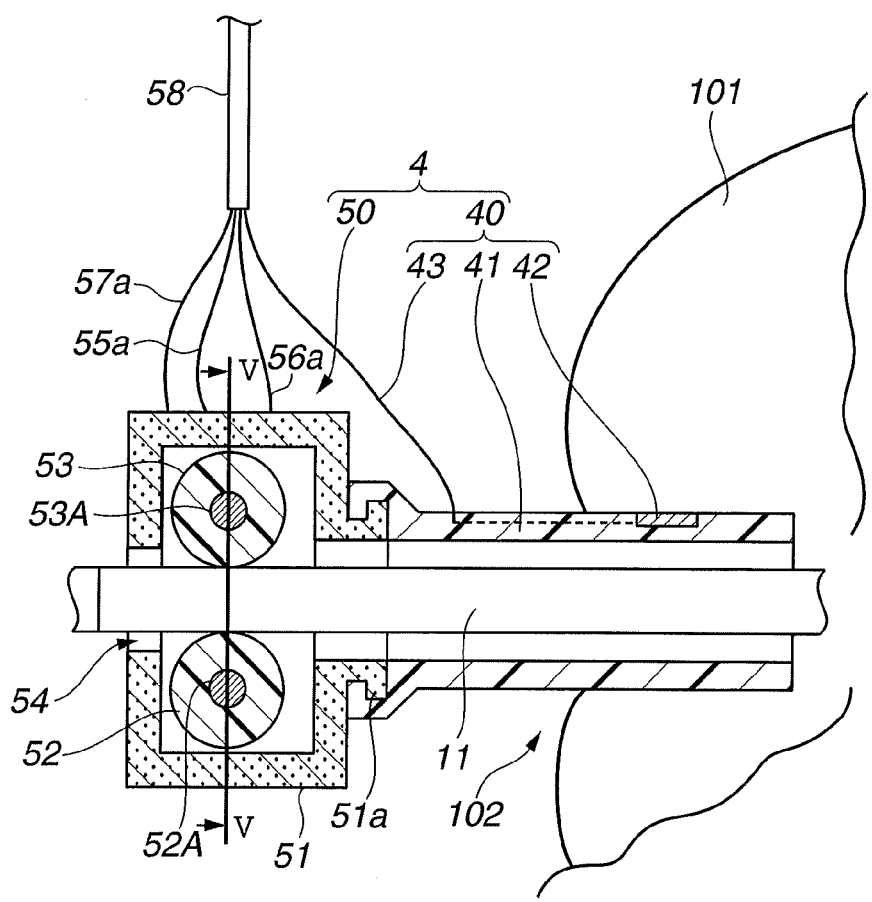

The anus fitting tool 4 includes, as shown in FIG. 4, a guide tube 40, and an insertion portion advancing/retracting apparatus 50.

The guide tube 40 is one of the medical action information detection sections, and includes a tube body 41, at least one pressure sensor 42, and a signal wire 43. The signal wire 43 is extended from the tube body 41 and connected to the determination control apparatus 7 as shown in FIG. 1.

The tube body 41 has a through hole through which the insertion portion 11 can be inserted. The tube body 41 is formed of an elastic tubular member such as a silicone tube. The tube body 41 is set in an anus 102 of a patient 101.

The pressure sensor 42 is provided on an outer circumference of the tube body 41. The pressure sensor 42 is a patient pressure sensor, and a living body information detection section for obtaining living body information. The pressure sensor 42 detects an anal contraction force of the patient as medical action information. Specifically, the guide tube 40 is placed in a predetermined position in the anus 102 of the patient 101 as shown in FIG. 4 by a doctor or a medical worker so that the patient pressure sensor 42 can reliably detect an anal contraction force. A detection value of the patient pressure sensor 42 is outputted via the signal wire 43 to the determination control apparatus 7.

Figure 5:
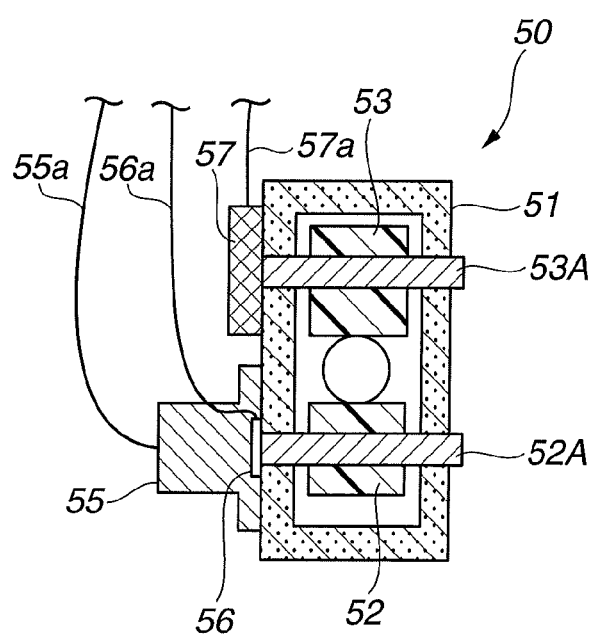

An insertion portion advancing/retracting apparatus 50 is provided on a proximal end side of the guide tube 40 as shown in FIGS. 4 and 5. In this embodiment, an end of the tube body 41 is mounted to a connecting portion 51a.

The insertion portion advancing/retracting apparatus 50 also serves as a medical instrument control apparatus and an insertion portion movement amount detection apparatus. The insertion portion advancing/retracting apparatus 50 includes two rotatable rollers 52 and 53 in an inner space of a casing 51. The casing 51 has, in one of facing sides, an insertion portion insertion port 54 through which the insertion portion 11 is inserted. A connecting portion 51a is formed on the other side of the casing 51. The connecting portion 51a has a communication hole that provides communication between inside and outside of the casing 51. The insertion portion 11 introduced through the insertion portion insertion port 54 into the casing 51 is led out through the communication hole.

The two rollers 52 and 53 each are formed of an elastic resin member or rubber member. The roller 52 is integrally secured to a rotating shaft 52A. The roller 53 is integrally secured to a rotating shaft 53A. The insertion portion 11 inserted through the insertion portion insertion port 54 is held between the rollers 52 and 53 with an outer surface thereof being pressed by the rollers 52 and 53.

The rotating shaft 52A is a drive shaft. One end of the rotating shaft 52A is connected via a clutch 56 to a motor 55 provided outside the casing 51. Thus, the roller 52 can be switched between a state of being rotated clockwise or counterclockwise by a drive force of the motor 55 and a state of being rotated by movement of the insertion portion 11. The insertion portion 11 pressed and held between the rollers 52 and 53 is advanced or retracted by rotation of the roller 52 by the drive force of the motor 55.

The rotating shaft 53A is a driven shaft. One end of the rotating shaft 53A is provided in an encoder 57 placed outside the casing 51. The encoder 57 is a driving state detection section. The encoder 57 is one of the medical action information detection sections. The encoder 57 detects, from a rotation amount of the rotating shaft 53A, a movement amount of the flexible tube portion 11c as a parameter by driving of the insertion portion advancing/retracting apparatus 50 that is one of medical action information. The detection value of the encoder 57 is outputted via a signal wire 57a to the determination control apparatus 7 as an insertion portion movement amount.

Reference numeral 55a denotes a motor signal wire. Reference numeral 56a denotes a clutch signal wire. The signal wires 55a and 56a are connected to the determination control apparatus 7.

In this embodiment, the signal wire 43 extended from the patient pressure sensor 42, the motor signal wire 55a, the clutch signal wire 56a, and the encoder signal wire 57a are collectively inserted through a signal wire cable 58.

In this embodiment, the insertion portion 11 of the endoscope 1 is inserted into a large intestine through between the rollers 52 and 53 in the insertion portion advancing/retracting apparatus 50 and the through hole in the guide tube 40. Thus, when the insertion portion 11 is inserted into the large intestine, the roller 53 is rotated with movement of the flexible tube portion 11c. At this time, the encoder 57 detects the rotation amount of the rotating shaft 53A rotated by the rotation of the roller 53 as a movement amount of the flexible tube portion 11c.

Meanwhile, the motor 55 of the insertion portion advancing/retracting apparatus 50 is driven by a control signal being outputted from the determination control apparatus 7 to the insertion portion advancing/retracting apparatus 50. The motor 55 is driven to rotate the roller 52 secured to the rotating shaft 52A as the drive shaft. Then, the insertion portion 11 held between the rollers 52 and 53 is advanced or retracted. An advance amount or a retraction amount, that is, an insertion portion movement amount of the insertion portion 11 is detected by the encoder 57.

The endoscope 1 and the determination control apparatus 7 are connected to the endoscope control apparatus 6. The endoscope control apparatus 6 mainly includes a control section 61 having a CPU therein, a storage apparatus 62, for example, a hard disk as a storage section, a signal processing section 63, a calculation processing section 64, or the like. Reference numeral 65 denotes a light source section, which controls an illumination state of an illuminating light that illuminates an inside of the body cavity.

Various thresholds are registered in the storage apparatus 62 as reference information used for determination of the determination control apparatus 7. In this embodiment, a threshold of an anal contraction force and a threshold of an insertion portion grasping force are registered in the storage apparatus 62. The thresholds are outputted to the determination control apparatus 7.

The threshold of the insertion portion grasping force is set based on grip strength of the lower doctor 104. The threshold of the anal contraction force is set in view of physical features of the patient, a technical level of the lower doctor 104, or the like. The physical features include age, sex, health condition, or the like. The thresholds are registered in the storage apparatus 62 by the upper doctor 103.

The signal processing section 63 performs signal processing of generating a control signal that drives an image pickup device provided in the endoscope 1, and a video signal from an electric signal transmitted from the image pickup device. The video signal generated by the signal processing section 63 is outputted via the determination control apparatus 7 to the screen 5a of the endoscope monitor 5. An endoscopic image displayed on the screen 5a is observed by the upper doctor 103 and the lower doctor 104.

A calculation processing section 64 is one of the medical action information detection sections. The calculation processing section 64 measures an advancing/retracting movement amount of the distal end portion as an actual operation result by the lower doctor 104 that is one of medical action information based the video signal generated by the signal processing section 63. The advancing/retracting movement amount calculated by the calculation processing section 64 is a movement amount of the distal end portion 11a in the body. The movement amount of the distal end portion 11a is a movement amount measured by comparing the current endoscopic image with an endoscopic image obtained a predetermined time before, and is outputted as a distal end portion movement amount to the determination control apparatus 7.

As shown in FIG. 1, the determination control apparatus 7 is a switching signal generation apparatus including a determination section 71, a signal output switching section 72, a signal/information conversion section 73, and a control instruction section 74.

To the determination section 71, various medical action information is inputted such as a value of the anal contraction force detected by the patient pressure sensor 42, the distal end portion movement amount measured from the endoscopic image, the insertion portion movement amount detected by the encoder 57, and a value of the insertion portion grasping force detected by the operator pressure sensor 22. To the determination section 71, the threshold of the anal contraction force and the threshold of the insertion portion grasping force are inputted that are medical action information thresholds and registered in the storage apparatus 62.

When the values are inputted to the determination section 71, the determination section 71 compares the value of the anal contraction force with the threshold thereof, compares the value of the distal end portion movement amount with the value of the insertion portion movement amount, and compares the value of the insertion portion grasping force with the threshold thereof.

Figures 6, 7:
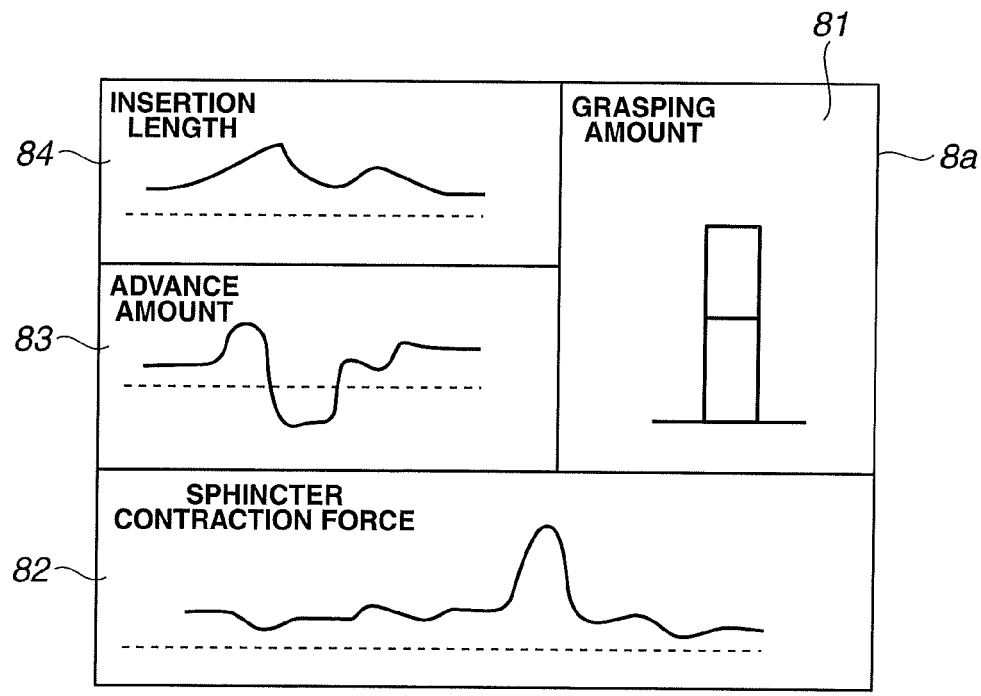

Then, the determination section 71 compares the threshold of the anal contraction force with the anal contraction force detected by the patient pressure sensor 42, and determines presence/absence of a load on the patient. Specifically, as shown in FIG. 6, when the anal contraction force detected by the patient pressure sensor 42 is smaller than the threshold thereof, it is determined that a patient's condition is good ("1" in the drawing), and when the anal contraction force detected by the patient pressure sensor 42 is larger than the threshold thereof, it is determined that there is a load on the patient ("2" in the drawing).

The determination section 71 determines whether the distal end portion movement amount matches the insertion portion insertion amount, and determines whether the insertion portion is smoothly introduced into the body. Specifically, as shown in FIG. 6, when the distal end portion movement amount matches the insertion portion insertion amount, it is determined that the insertion portion 11 is smoothly inserted into the body ("1" in the drawing), and when the distal end portion movement amount is different from the insertion portion insertion amount, specifically, when the distal end portion movement amount is smaller than the insertion portion insertion amount, it is determined that the distal end portion 11a is caught on a wall or it takes time to insert the insertion portion 11 because of a sharp loop or the like ("2" in the drawing).

The determination section 71 also compares the threshold of the insertion portion grasping force with the insertion portion grasping force detected by the operator pressure sensor 22, and determines whether an insertion procedure of the operator is satisfactory. Specifically, as shown in FIG. 6, when the insertion portion grasping force detected by the operator pressure sensor 22 is smaller than the threshold thereof, it is determined that the insertion procedure is satisfactorily performed ("1" in the drawing), and when the insertion portion grasping force detected by the operator pressure sensor 22 is larger than the threshold thereof, it is determined that it takes time to insert the insertion portion 11 and too strong a force is applied ("2" in the drawing).

Next, the signal output switching section 72 will be described.

The signal output switching section 72 includes an input section 72a, a switching section 72b, a first output section 72c, and a second output section 72d.

To the input section 72a, the control instruction signal outputted from the controller 3 is inputted. The switching section 72b is a so-called switch that switches an output destination of the control instruction signal inputted to the input section 72a to the first output section 72c or the second output section 72d. The switching section 72b switches the output destination based on a switching signal described later outputted from the control instruction section 74.

The first output section 72c is connected to the signal/information conversion section 73, and outputs the control instruction signal transmitted via the switching section 72b to the signal/information conversion section 73. Meanwhile, the second output section 72d is connected to the insertion portion advancing/retracting apparatus 50, and outputs the control instruction signal transmitted via the switching section 72b to the motor 55.

To the signal/information conversion section 73, the video signal outputted from the endoscope control apparatus 6, the control instruction signal outputted from the controller 3, and various medical action information inputted to the determination section 71 are inputted.

The value of the anal contraction force detected by the patient pressure sensor 42 inputted to the signal/information conversion section 73, the distal end portion movement amount measured from the endoscopic image, the insertion portion movement amount detected by the encoder 57, and the value of the insertion portion grasping force detected by the operator pressure sensor 22 are outputted to the detection monitor 8 in real time.

The detection monitor 8 is a display apparatus that is observed by the upper doctor 103 for understanding a situation of the insertion procedure of the lower doctor 104. As shown in FIG. 7, a screen 8a as an information display section of the detection monitor 8 displays, for example, a grasping force display area 81 that displays lower doctor operation information, a sphincter contraction force area 82 that displays patient information, an advance amount area 83 that displays medical instrument operation information, and an insertion length area 84 that displays medical instrument operation information.

On the grasping force display area 81 of the screen 8a, the value of the insertion portion grasping force is displayed, for example, in bar chart. Meanwhile, the value of the anal contraction force is displayed on the sphincter contraction force area 82, for example, in time-sequential line chart. The distal end portion movement amount is displayed on the advance amount area 83 as a movement amount per unit time, for example, in time-sequential line chart. The insertion portion movement amount is displayed on the insertion length area 84 as a movement amount per unit time, for example, in time-sequential line chart. The unit time for measuring the insertion portion movement amount is equal to a predetermined time when the current endoscopic image and an endoscopic image obtained a predetermined time before are compared in measurement of the distal end portion movement amount.

In this embodiment, the obtained medical action information is displayed in the bar chart and the line charts. However, the obtained medical action information may be displayed on the areas by specific numerical values. In addition to the grasping force display area 81, the sphincter contraction force area 82, the advance amount area 83, and the insertion length area 84, the detection monitor 8 may include a determination result display area that displays the determination results of the determination section 71 shown in FIG. 6 or an endoscopic image area that displays an endoscopic image.

The video signal inputted to the signal/information conversion section 73 is outputted to the endoscope monitor 5 and displayed on the screen 5a as an endoscopic image.

The control instruction signal of the controller 3 is inputted to the signal/information conversion section 73 and then converted into character information, and displayed together with the endoscopic image on the screen 5a of the endoscope monitor 5. Specifically, for example, when the upper doctor 103 tilts the operation lever 35 substantially 15 degrees to the distal end side, the signal/information conversion section 73 outputs an operation instruction "Carefully advance insertion portion" previously set from the inputted control instruction signal to the endoscope monitor 5. Thus, the operation instruction is displayed on a predetermined position on the screen 5a.

The operation instruction displayed on the screen 5a is not limited to the above-described instruction, but various operation instructions are displayed on the screen 5a. The operation instructions include, for example, an operation instruction "Carefully retract insertion portion" when the upper doctor 103 tilts the operation lever 35 substantially 15 degrees to the proximal end side, an operation instruction "Advance insertion portion" when the upper doctor 103 tilts the operation lever 35, 45 degrees to the distal end side, an operation instruction "Stop insertion" when the upper doctor 103 tilts the operation lever 35 from one tilt direction to the other direction, that is, the opposite direction, an operation instruction "Continue procedure" when the upper doctor 103 does not operate the operation lever 35, or release his/her hand to switch the operation lever 35 from the tilted state to an upright state, or the like.

The control instruction section 74 determines the procedure situation of the lower doctor based on each determination result of the determination section 71, and outputs a switching signal corresponding to the determination result to the signal output switching section 72.

Specifically, the control instruction section 74 checks combinations of the determination results, and when all the determination results of the determination section 71 are "1" as shown in FIG. 6, the control instruction section 74 determines that the procedure of the lower doctor 104 progresses satisfactorily (procedure situation "1" in the drawing). Meanwhile, when all the determination results of the determination section 71 are "2", the control instruction section 74 determines that the procedure of the lower doctor 104 is unstable (procedure situation "2" in the drawing). When two of the determination results are "1" and one of the determination results is "2" as shown in FIG. 6, the control instruction section 74 determines that the procedure of the lower doctor 104 is satisfactory. When one of the determination results is "1" and two of the determination results are "2", the control instruction section 74 determines that the procedure of the lower doctor 104 is unstable.

When the control instruction section 74 determines that the procedure situation is satisfactory, the control instruction section 74 outputs a first switching signal to the signal output switching section 72. Then, the switching section 72b is connected to the first output section 72c. Thus, the control instruction signal of the controller 3 is inputted to the input section 72a, and then outputted to the signal/information conversion section 73.

Meanwhile, when the control instruction section 74 determines that the procedure situation is unstable, the control instruction section 74 outputs a second switching signal to the signal output switching section 72. Then, the switching section 72b is connected to the second output section 72d. Thus, the control instruction signal of the controller 3 is inputted to the input section 72a, and then outputted to the insertion portion advancing/retracting apparatus 50. Then, the clutch 56 of the motor 55 of the insertion portion advancing/retracting apparatus 50 is engaged, then driving of the motor 55 is started, and the insertion portion 11 is advanced/retracted by rotation of the roller 52. At this time, a comment "Upper doctor performs operation from here" or the like is displayed on the screen 5a to notify the lower doctor 104 of switching to the operation of the upper doctor 103.

In this embodiment, connection between the apparatuses is so-called wired connection such that the determination control apparatus 7 and the insertion portion grasping grip 2 are connected by the signal wire 23, and the determination control apparatus 7 and the controller 3 are connected by the signal wire 33. The connection between the apparatuses is not limited to the wired connection, but may be wireless connection.

In this embodiment, the determination control apparatus 7 and the endoscope control apparatus 6 are separately formed. However, the endoscope control apparatus 6 and the determination control apparatus 7 may be integrally formed.

A case will be described where large intestine endoscopy is performed using the medical system 10 configured as described above.

When the upper doctor 103 and the lower doctor 104 perform large intestine endoscopy, the upper doctor 103 grasps the controller 3, and waits in a position where the upper doctor 103 can visually identify the screen 5a of the monitor 5 and the screen 8a of the monitor 8.

Meanwhile, the lower doctor 104 checks a placement state of the anus fitting tool 4, particularly, a setting position or the like of the guide tube 40. Then, after the checking, the lower doctor 104 starts the procedure.

First, the lower doctor 104 fits the insertion portion grasping grip 2 to the insertion portion 11. The lower doctor 104 also inserts the distal end portion 11a of the insertion portion 11 into the casing 51 of the insertion portion advancing/retracting apparatus 50 through the insertion portion insertion port 54 formed in the casing 51. Then, the lower doctor 104 places the insertion portion 11 between the rollers 52 and 53, and the distal end portion 11a is led out from the through hole in the connecting portion 51a. Thus, the distal end portion 11a of the insertion portion 11 is placed in the tube body 41.

Then, the insertion procedure into the large intestine by the lower doctor 104 is started. Specifically, the lower doctor 104 grasps the insertion portion 11 via the insertion portion grasping grip 2. Then, the lower doctor 104 checks the operation instruction from the upper doctor 103 displayed on the screen 5a, and starts the procedure according to the operation instruction displayed on the screen 5a.

Figure 8:
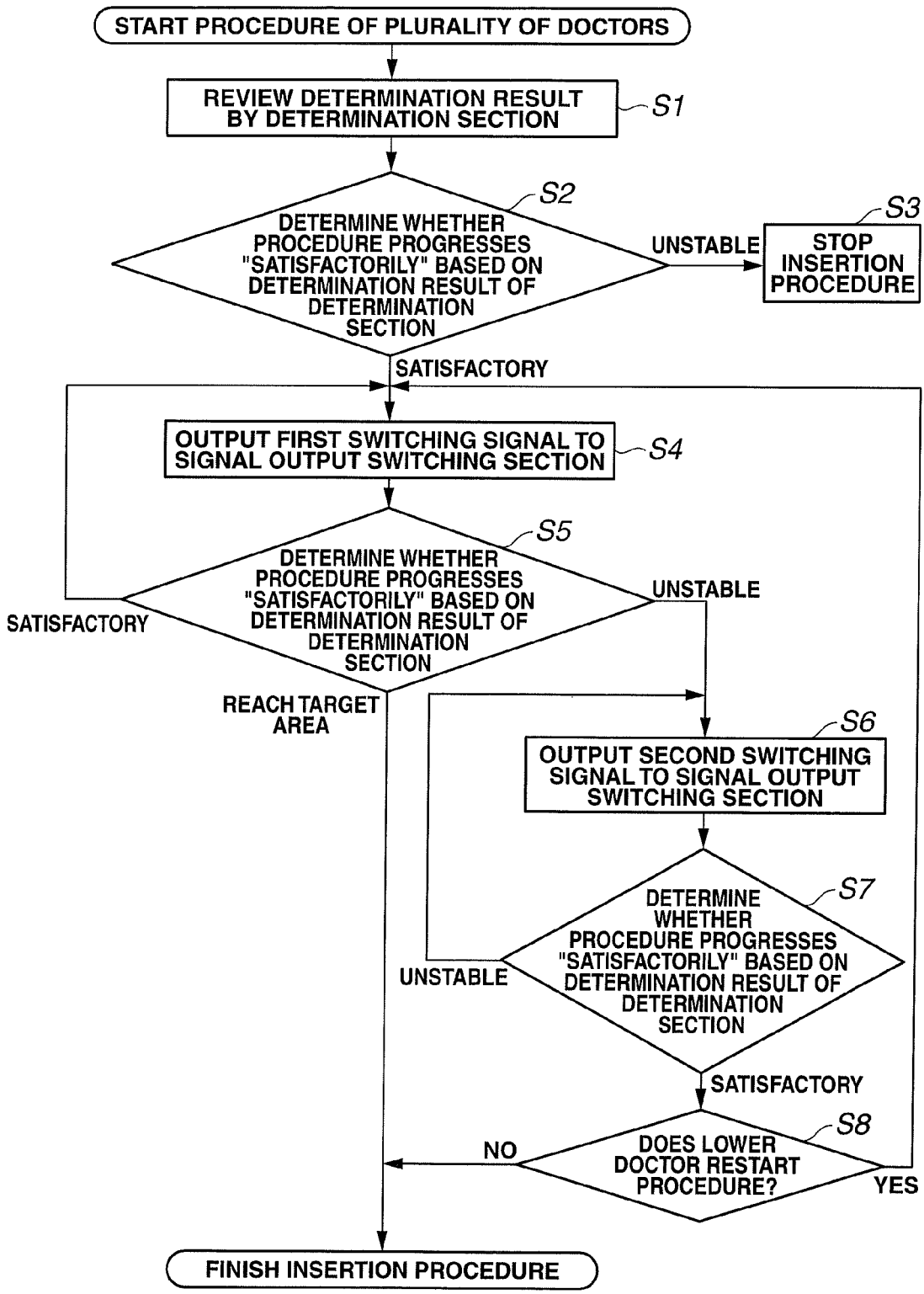

The control instruction section 74 starts reviewing the determination result of the determination section 71 to determine whether the insertion procedure of the lower doctor 104 is satisfactory based on the determination result of the determination section 71 as shown in Step S1 in FIG. 8, and proceeds to Step S2.

The upper doctor 103 grasps the controller 3, and checks an endoscopic image displayed on the screen 5a and information displayed on the display areas 81, 82, 83 and 84 of the screen 8a to understand the operation situation of the lower doctor 104.

In Step S2, the control instruction section 74 determines whether the procedure is "satisfactory" or "unstable" based on the determination result of the determination section 71. Then, the control instruction section 74 outputs a switching signal corresponding to the determination result to the signal output switching section 72.

When the control instruction section 74 determines that the procedure is "unstable" although immediately after the start of the procedure, the control instruction section 74 proceeds to Step S3 and stops the insertion procedure. At this time, the control instruction section 74 displays a comment, for example, "Please check" on the screen 5a via the signal/information conversion section 73 and encourages checking.

Meanwhile, when the control instruction section 74 determines that the procedure is "satisfactory", the control instruction section 74 proceeds to Step S4, and outputs a first switching signal to the signal output switching section 72 and proceeds to Step S5.

In Step S4, the first switching signal is outputted from the control instruction section 74 to the signal output switching section 72. Thus, when the upper doctor 103 grasps the controller 3 without operating the operation lever 35, the screen 5a displays an operation instruction "Continue procedure". Meanwhile, when the upper doctor 103 tilts the operation lever 35, for example, substantially 45 degrees to the distal end side, the screen 5a displays an operation instruction "Advance insertion portion".

The lower doctor 104 checks the operation instruction from the upper doctor 103 displayed on the screen 5a, and then starts the procedure. At the start of the insertion procedure, the insertion portion 11 is placed in the tube body 41. Thus, the insertion portion 11 is smoothly advanced in the tube body 41 by a hand operation of the lower doctor 104. Then, the insertion portion 11 is advanced in the tube body 41 and brought close to a rectum, and thus an endoscopic image of the rectum is displayed on the screen 5a.

At this time, for example, when the upper doctor 103 tilts the operation lever 35 substantially 15 degrees to the distal end side, the screen 5a displays an endoscopic image of the rectum and an operation instruction "Carefully advance insertion portion".

The lower doctor 104 carefully introduces the insertion portion 11 into the rectum according to the instruction displayed on the screen 5a.

The upper doctor 103 checks the introduction of the insertion portion 11 into the rectum, and then continues understanding the operation situation of the lower doctor 104 from the screen 5a, the screen 8a, or the like, and operates the operation lever 35 correspondingly to the procedure.

The control instruction section 74 outputs the first switching signal to the signal output switching section 72 while determining that the procedure is "satisfactory". Thus, the screen 5a displays the endoscopic image and the operation instruction from the upper doctor 103. Specifically, the screen 5a displays operation instructions such as "Do not continue procedure", "Advance insertion portion", "Stop insertion", "Carefully retract insertion portion", or the like. Thus, the lower doctor 104 can continue the procedure while checking the instruction displayed on the screen 5a.

Then, when the insertion portion 11 reaches a target area, the insertion procedure is finished. Then, a large intestine test is performed by the upper doctor 103 or the lower doctor 104.

If the upper doctor 103 switches the operation lever 35 from a state of an advance instruction to a state of a retraction instruction during the procedure of the lower doctor 104, the controller 3 outputs an instruction "Stop insertion". At this time, in the case where the control instruction section 74 determines that the procedure is "satisfactory", the control instruction section 74 proceeds to Step 4. Thus, the screen 5a displays the instruction "Stop insertion". The lower doctor 104 once stops the insertion of the insertion portion 11 according to the instruction displayed on the screen 5a. Then, the lower doctor 104 restarts the procedure according to the instruction by the upper doctor 103.

Meanwhile, in the case where the control instruction section 74 determines that the procedure is "unstable" when the upper doctor 103 outputs the instruction "Stop insertion", the control instruction section 74 proceeds to Step S6. In Steps S6, the control instruction section 74 notifies the stop of the insertion procedure of the lower doctor 104, outputs the second switching signal to the signal output switching section 72, and proceeds to Step S7. At this time, the screen 5a displays a comment, for example "Upper doctor performs operation from here".

In Step S6, the second switching signal is outputted to the signal output switching section 72, and thus a control signal for a retraction instruction that is the control instruction signal inputted from the upper doctor controller 3 to the input section 72a is outputted to the motor 55 of the insertion portion advancing/retracting apparatus 50. Then, the clutch 56 is engaged, the roller 52 is rotated by the drive force of the motor 55, and the insertion portion 11 is retracted by the rotation of the roller 52, thereby resolving the unstable situation.

When changes occur such that the insertion portion grasping force of the lower doctor 104 is reduced, the anal contraction force of the patient is reduced, or the insertion portion movement amount matches the distal end portion movement amount, and the control instruction section 74 again determines that the procedure is "satisfactory" while the control instruction signal of the upper doctor 103 is outputted to the motor 55, the control instruction section 74 proceeds to Step S8.

In Step S8, the control instruction section 74 checks whether the procedure of the lower doctor 104 is restarted. Specifically, instead of the comment "Upper doctor performs operation from here" displayed on the screen 5a, a comment "Does lower doctor restart procedure?" is displayed.

When the upper doctor 103 allows restart of the insertion procedure of the lower doctor 104, the operation lever 35 is operated so that the screen 5*a* displays "Carefully advance insertion portion". Then, the control instruction section 74 proceeds to Step S4, outputs the first switching signal to the signal output switching section 72, and restarts the procedure of the lower doctor 104.

Meanwhile, when the upper doctor 103 determines that it is difficult to continue the insertion procedure of the lower doctor 104, for example, the determination control apparatus 7 is powered off, and the upper doctor 103 replaces the lower doctor 104 and restarts the insertion procedure.

As such, the endoscope system including the medical instrument that can be operated by the upper doctor and the lower doctor includes the upper doctor controller and the determination control apparatus. Thus, the upper doctor can operate the upper doctor controller and give an operation instruction to the lower doctor while the determination control apparatus determines that the procedure of the lower doctor is satisfactory.

Meanwhile, when the determination control apparatus determines that the procedure is unstable, the control instruction signal outputted from the upper doctor controller by the operation of the upper doctor is outputted as a control signal to the medical instrument. Specifically, the upper doctor can perform an endoscope operation for resolving the unstable procedure situation of the lower doctor without troublesome work such as a shift from the upper doctor controller to the medical apparatus.

Then, when the operation of the upper doctor resolves the unstable procedure situation, and the determination control apparatus again determines that the procedure is satisfactory, the procedure of the lower doctor can be smoothly restarted without troublesome work such as a shift of the medical apparatus between the upper doctor and the lower doctor.

In terms of teaching an endoscope operation, thresholds of medical action information can be set appropriately in view of a technical level of the lower doctor. Thus, a training of a medical instrument operation can be provided with priority on safety of the patient under the supervision of the upper doctor by appropriately changing an acceptable range for each lower doctor.

A second embodiment of the present invention will be described with reference to FIGS. 9 to 18.

Figure 9:
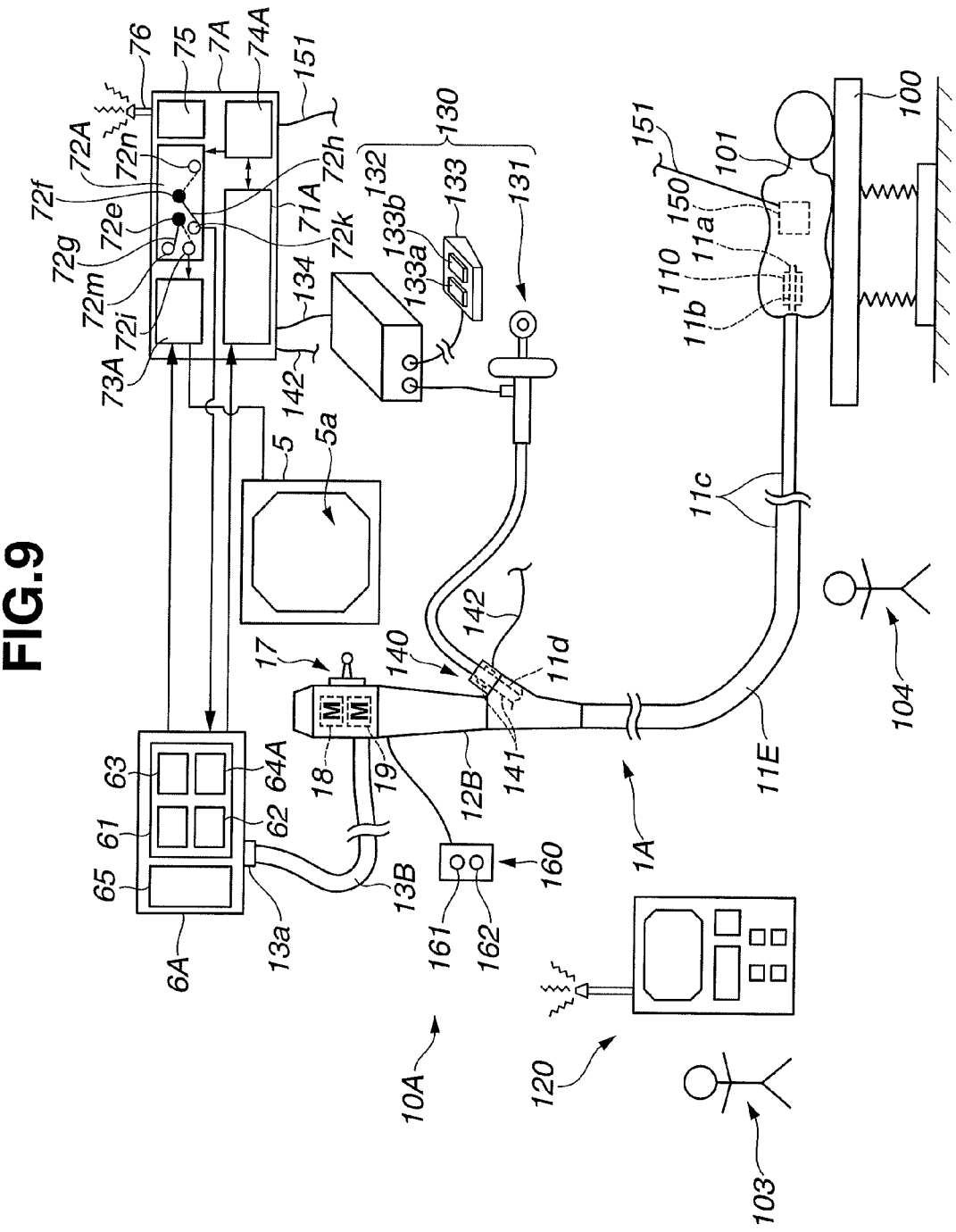
FIGS. 9 to 18 relate to a medical system according to a second embodiment of the present invention.
Figure 10:
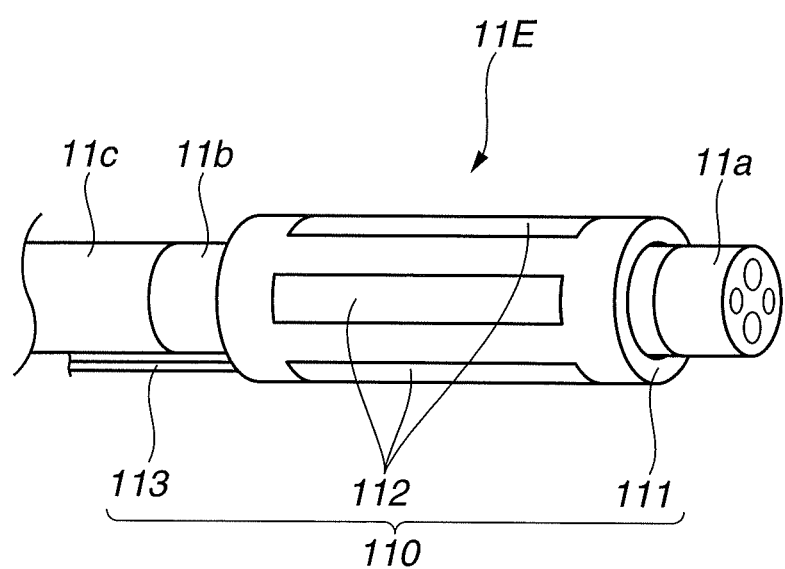
Figure 11:
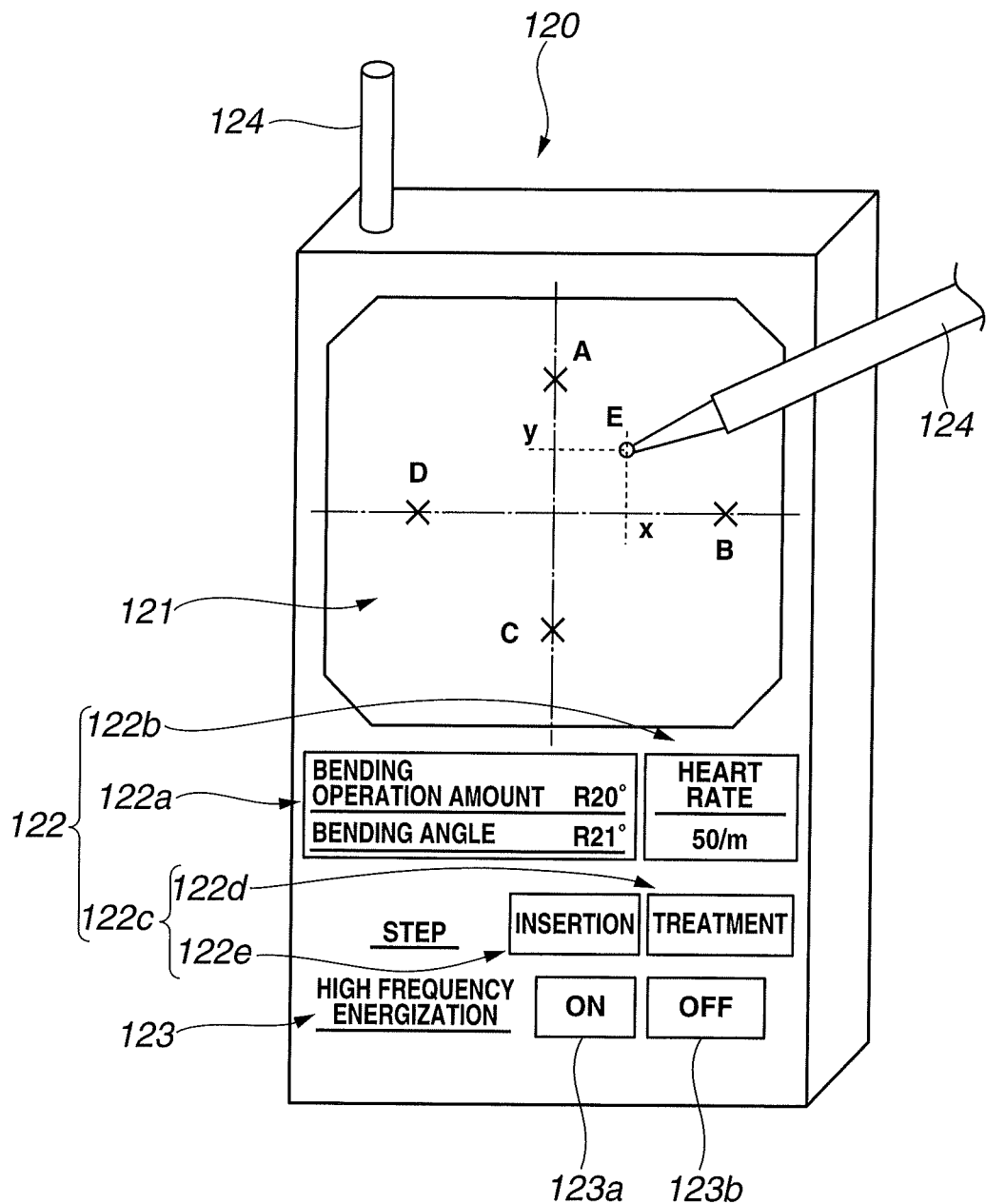
Figures 12, 13:
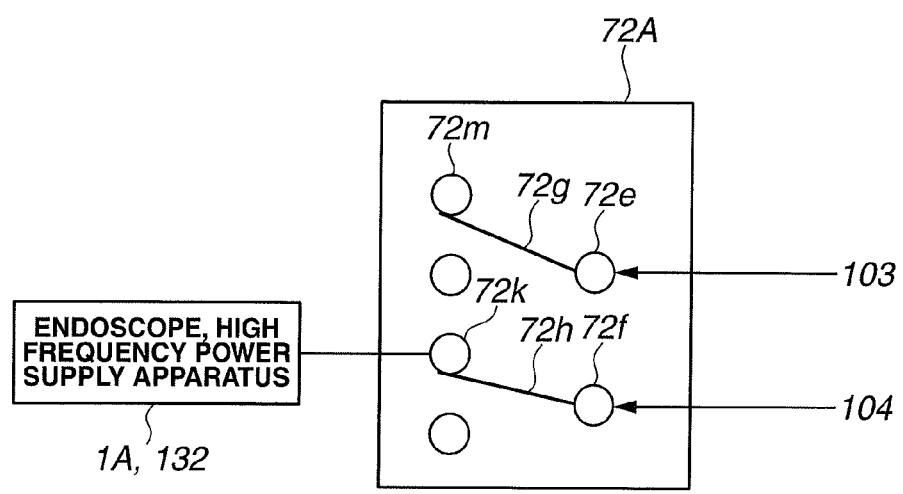
Figure 14:
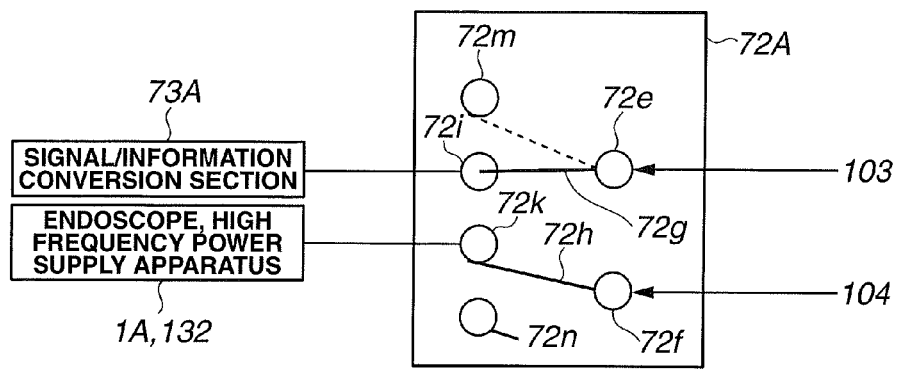
Figure 15:
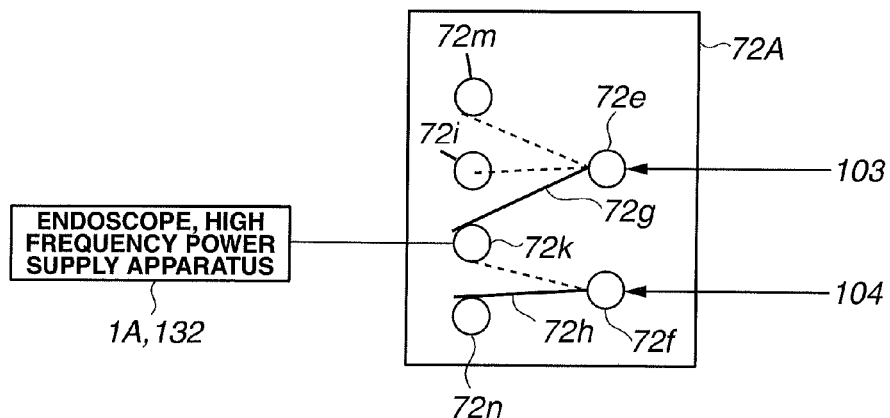
Figure 16:
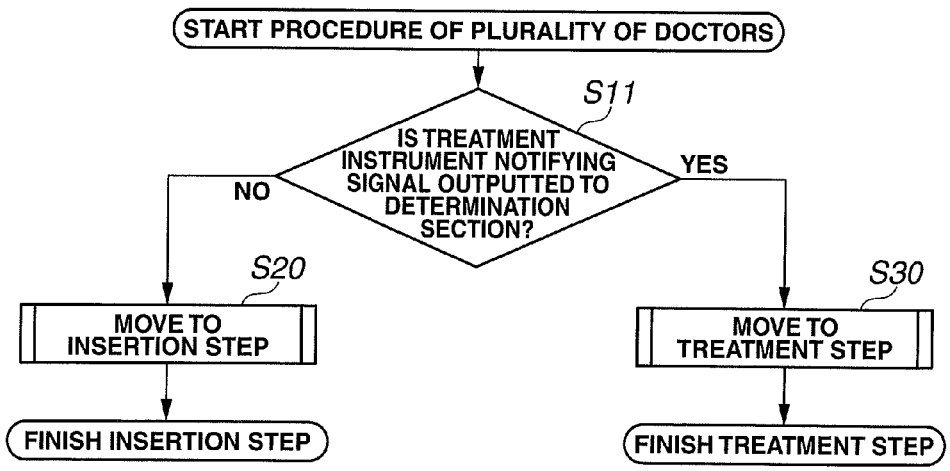
Figure 17:
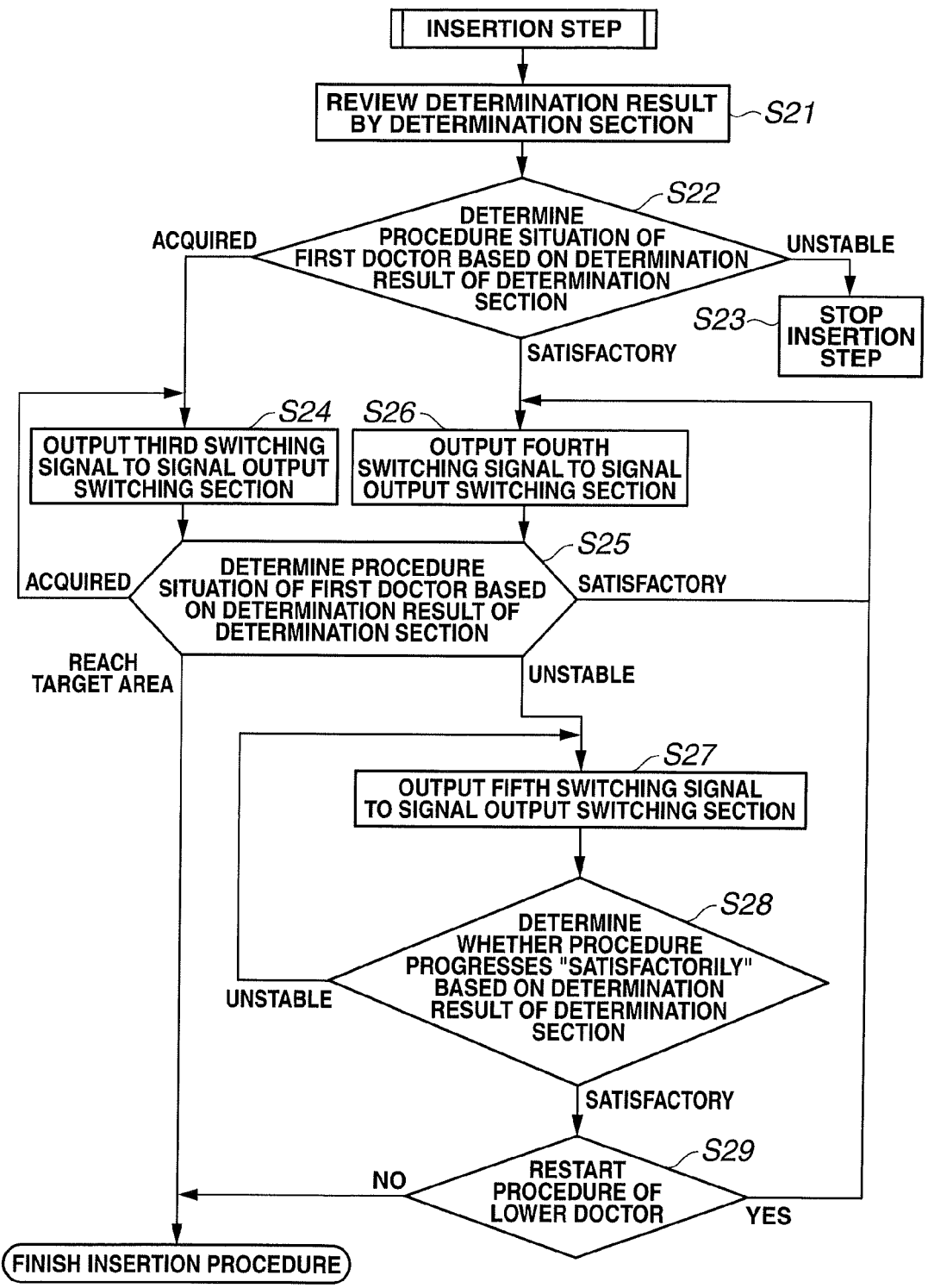
Figure 18:
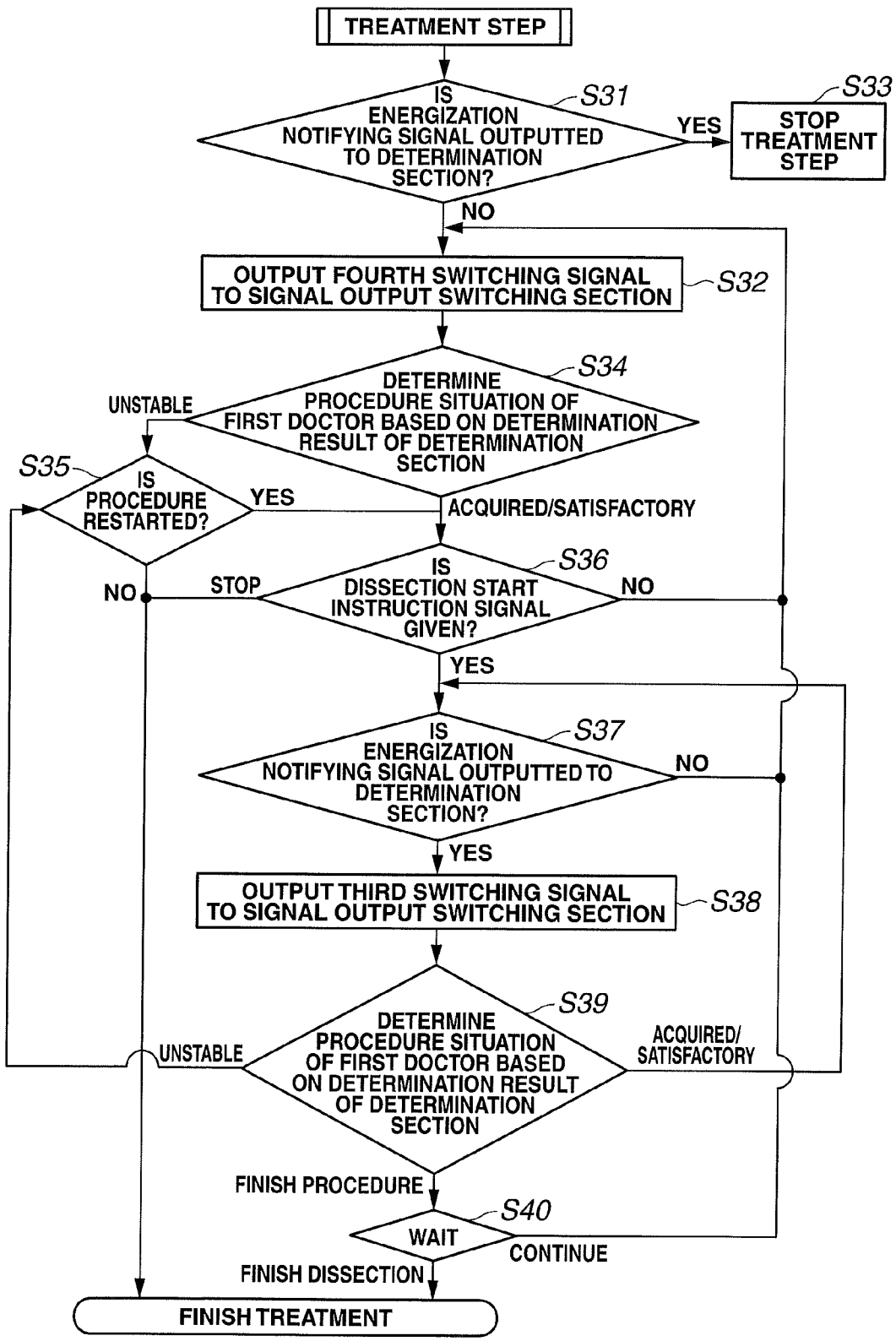

FIGS. 9 to 18 relate to a medical system according to the second embodiment of the present invention, FIG. 9 illustrates another configuration of an endoscope system, FIG. 10 illustrates a bending angle detection apparatus, FIG. 11 illustrates an upper doctor viewer, FIG. 12 illustrates a relationship between a determination result of a determination section and a switching signal outputted from a control instruction section, FIG. 13 illustrates a relationship between a switching section and an output section when a third switching signal is outputted from the control instruction section to a signal output switching section, FIG. 14 illustrates a relationship between the switching section and the output section when a fourth switching signal is outputted from the control instruction section to the signal output switching section, FIG. 15 illustrates a relationship between the switching section and an output section when a fifth switching signal is outputted from the control instruction section to the signal output switching section, FIG. 16 is a flowchart explaining an exemplary collaborative operation of an endoscope system by two doctors, FIG. 17 is a flowchart explaining an collaborative operation of an endoscope by two doctors in an insertion step, and FIG. 18 is a flowchart explaining a collaborative operation of an endoscope by two doctors in a treatment step.

In the second embodiment, the same components as in the first embodiment are denoted by the same reference numerals and descriptions thereof will be omitted.

As shown in FIG. 9, a medical system 10A of this embodiment includes an endoscope (hereinafter simply referred to as an electric bending endoscope) 1A having an electric bending function as a medical instrument, a bending portion bending angle detection apparatus 110, an upper doctor viewer (hereinafter simply referred to as a viewer) 120 as a second operation apparatus, a high frequency treatment apparatus 130, a treatment instrument detector 140, a heart rate meter 150, an endoscope monitor 5, an electric bending endoscope control apparatus 6A, and a determination control apparatus 7A.

The electric bending endoscope 1A is a so-called electronic endoscope including an image pickup device such as a CCD. The electric bending endoscope 1A includes an insertion portion 11E, an operation section 12B, and a universal cord 13B.

The insertion portion 11E includes a rigid distal end portion 11*a*, a bendable bending portion 11*b*, and a flexible tube portion 11*c* connected in order from a distal end side. The operation section 12B includes a bending lever 17. The bending lever 17 is a so-called joystick that can be tilted, and a lever tilt amount is detected by a position sensor. The bending lever 17 is of a home position return type that can be tilted, for example, in two axial directions toward a distal end side and a proximal end side parallel to a longitudinal axis of the operation section 12B, and right and left of the distal end side perpendicular to the longitudinally axis. In this embodiment, when a lower doctor uses the electric bending endoscope 1A, the bending lever 17 also serves as a first operation apparatus and a medical instrument control apparatus.

The bending portion 11*b* is configured so that a bending wire is pulled/slackened and bent by tilting the bending lever 17. In the operation section 12B, for example, two bending motors 18 and 19 and a sprocket (not shown) to which one end of the bending wire is secured. Then, the bending lever 17 is tilted, for example, to the proximal end side, a vertical bending wire secured to the sprocket is pulled/slackened by a drive force of the first bending motor 18, and the bending portion 11*b* is bent upward or downward. The second bending motor 19 is configured so that a lateral bending wire is pulled/slackened by a drive force of the second bending motor 19, and the bending portion 11*b* is bent leftward or rightward.

The operation section 12B is configured so that a treatment instrument detector 140 is provided at a treatment instrument insertion port 12*a*. The treatment instrument detector 140 is one of medical action information detection sections. The treatment instrument detector 140 includes an optical sensor 141 and a signal cable 142. The treatment instrument detector 140 has a through hole through which a treatment instrument is inserted, and the optical sensor 141 is provided in a predetermined position of the through hole. The optical sensor 141 is a light reflection sensor or a light transmission sensor, and a treatment instrument sensor that detects whether the treatment instrument is inserted through the treatment instrument insertion channel 11*d*. The signal cable 142 is connected to the determination control apparatus 7A. When the treatment instrument is inserted through the treatment instrument insertion channel 11*d* via the through hole in the treatment instrument detector 140, the treatment instrument detector 140 detects the insertion of the treatment instrument using the optical sensor 141, and outputs a treatment instrument notifying signal as medical action information to the determination control apparatus 7A.

A bending portion bending angle detection apparatus 110 is secured to an outer circumferential face of the bending portion 11b of the insertion portion 11E as shown in FIG. 10. The bending portion bending angle detection apparatus 110 is one of the medical action information detection sections. The bending portion bending angle detection apparatus 110 includes a grip body 111, a plurality of distortion sensors 112, and a signal cable 113 formed by collecting signal wires extended from the sensors 112. The signal cable 113 is extended to the outside, for example, along the insertion portion 11E, and connected to the electric bending endoscope control apparatus 6A.

The grip body 111 is a tube body such as a silicone tube having an elastic force and a small thickness. The grip body 111 is fitted to an outer circumferential face of the insertion portion 11E. Four distortion sensors 112 are provided correspondingly to upward, downward, leftward and rightward directions that are bending directions of the bending portion 11b. Specifically, the distortion sensors 112 are provided at 90 degree intervals in a circumferential direction so as to detect upward, downward, leftward and rightward bending angles. The distortion sensor 112 is a bending portion bending angle detection sensor. The distortion sensor 112 detects an electric signal for notifying a distortion amount. The distortion sensor 112 outputs a distortion amount as medical action information via each signal wire in the signal cable 113 to the electric bending endoscope control apparatus 6A.

In this embodiment, the bending portion bending angle detection apparatus 110 including the distortion sensor is provided at the bending portion 11b. However, the distortion sensor may be directly provided at the bending portion 11b.

As shown in FIG. 11, the viewer 120 includes a touch panel 121, a medical action information display section 122, and a high frequency switch 123. The viewer 120 includes an antenna 124 and an unshown communication section, and the determination control apparatus 7A and the viewer 120 are connected by wireless links so that the upper doctor can carry the viewer 120.

The high frequency switch 123 is an operation switch for selecting whether a high frequency current is passed through a high frequency treatment instrument (hereinafter referred to as an electrosurgical knife) 131 described later of the high frequency treatment apparatus 130. The high frequency switch 123 includes an ON button 123a for an instruction to pass the current, and an OFF button 123b for an instruction to stop passing the current.

The medical action information display section 122 substantially corresponds to the screen 8a of the detection monitor 8. The medical action information display section 122 includes, for example, a medical instrument operation information display section 122a that displays a bending operation amount and a bending portion bending angle, a patient information display section 122b that displays a heart rate, and a procedure information display section 122c. The procedure information display section 122c includes a treatment mode notifying section 122d and an insertion/test mode notifying section 122e. The treatment mode notifying section 122d notifies that the treatment instrument is inserted through the treatment instrument insertion channel 11d to perform treatment. The insertion/test mode notifying section 122e notifies that the treatment instrument is not inserted through the treatment instrument insertion channel 11d.

The touch panel 121 displays an endoscopic image displayed on the endoscope monitor 5, and can give an operation instruction using a stylus 125 as an input apparatus. Specifically, in an insertion/test mode, the touch panel 121 is divided into four parts, for example, as shown by dash-single-dot lines. When the stylus 125 presses and indicates near a point A, the screen 5a displays an operation instruction "Upward bending". When the stylus 125 presses and indicates near a point B, the screen 5a displays an operation instruction "Rightward bending". When the stylus 125 presses and indicates near a point C, the screen 5a displays an operation instruction "Downward bending". When the stylus 125 presses and indicates near a point D, the screen 5a displays an operation instruction "Leftward bending". When the dash-single-dot lines are an X axis and a Y axis, and the stylus 125 presses and indicates, for example, a point E in a first quadrant as shown, an operation instruction "Upward bending of x degrees and rightward bending of y degrees" or the like is displayed from an XY coordinate of the point E.

Similarly, when the stylus 125 indicates, for example, a point in a second quadrant, an operation instruction "Upward bending of x degrees and leftward bending of −y degrees" is displayed. The touch panel 121 can display an operation instruction list (not shown) having a plurality of instructions, for example, "Stop", "Finish", "Restart", "Change doctor", "Move to dissection of next polyp", or the like. An operation instruction is appropriately selected from the operation instruction list by the stylus 125, thereby allowing the operation instruction to be displayed on the screen 5a.

In the treatment mode, the upper doctor 103 can trace the touch panel 121 displaying the endoscopic image using the stylus 125, and indicate a dissection line for resecting the polyp on the screen 5a to give an instruction.

In the insertion/test mode, when an upper doctor switching section (see reference numeral 72g in FIG. 9) described later is connected to a second output section (see reference numeral 72k in FIG. 9) described later, and the upper doctor 103 presses and indicates a point on the touch panel 121, information on the pressed and indicated point is outputted as an operation instruction signal for bending the bending portion 11b of the electric bending endoscope 1A.

As shown in FIG. 9, the high frequency treatment apparatus 130 includes an electrosurgical knife 131, a high frequency power supply apparatus 132, and a foot switch 133. The foot switch 133 includes an energization switch 133a that supplies a high frequency current to the electrosurgical knife 131, and an OFF switch 133b that stops supply of the high frequency current.

The high frequency power supply apparatus 132 is one of the medical action information detection sections. The high frequency power supply apparatus 132 outputs a high frequency current, and the electrosurgical knife 131 and the foot switch 133 are connected thereto. The electrosurgical knife 131 can dissect living tissue by receiving the high frequency current supplied from the high frequency power supply apparatus 132. The high frequency power supply apparatus 132 is connected via a signal wire 134 to the determination control apparatus 7A. The high frequency power supply apparatus 132 outputs an energization notifying signal as medical action information for notifying the determination control apparatus 7A of treatment with the electrosurgical knife 131 being performed when the energization switch 133a of the foot switch 133 is operated.

A heart rate meter 150 is one of the medical action information detection sections, and has a living body information detection section. The heart rate meter 150 is fitted to a predetermined position near a heart of the patient to detect the patient's heart rate as living body information. A detection value of the heart rate meter 150 is outputted as medical action information via a signal wire 151 to the determination control apparatus 7A.

To the endoscope control apparatus 6A, the electric bending endoscope 1A and the determination control apparatus 7A are connected. The endoscope control apparatus 6A mainly includes therein a control section 61, a storage apparatus 62, a signal processing section 63, a calculation processing section 64A, or the like. Reference numeral 65 denotes a light source section, which controls an illumination state of an illuminating light that illuminates an inside of the body cavity.

Various thresholds used for determination of the determination control apparatus 7A are registered in a storage apparatus 62. Medical action information thresholds registered in the storage apparatus 62 are a threshold of the patient's heart rate and a threshold of a frequency of a bending lever operation. The thresholds are outputted to the determination control apparatus 7A. The thresholds are values set appropriately as in the above-described embodiment.

The signal processing section 63 performs signal processing or the like for generating a control signal for driving the image pickup device provided in the electric bending endoscope 1A, and a video signal. The video signal generated by the signal processing section 63 is outputted via the determination control apparatus 7A to the screen 5a of the endoscope monitor 5 and the viewer 120.

The calculation processing section 64A is one of the medical action information detection sections. The calculation processing section 64A calculates a bending operation angle and a bending portion bending angle as medical action information and outputs the angles to the determination control apparatus 7. Specifically, the calculation processing section 64A calculates the bending operation angle from a bending operation signal outputted when the bending lever 17 is tilted. The bending operation signal includes a signal for notifying a tilt angle outputted from a position sensor, and a signal for notifying a tilt direction. The calculation processing section 64A calculates a bending portion bending angle including a bending direction and a bending angle of the bending portion 11b from a distortion amount as a detection value of each distortion sensor 112.

Further, when the bending operation angle of the bending lever 17 calculated by the calculation processing section 64A is inputted via a second output section 72k described later to the calculation processing section 64A, the calculation processing section 64A generates drive signals for driving the motors 18 and 19 and outputs the signals to the motors 18 and 19. Also, as described above, when the touch panel 121 is pressed and indicated and thus the operation instruction signal outputted from the viewer 120 is inputted via the second output section 72k to the calculation processing section 64A, the calculation processing section 64A generates drive signals for driving the motors 18 and 19 and outputs the signals to the motors 18 and 19.

The calculation processing section 64A counts the number of operations of the bending lever 17 by the doctor.

As shown in FIG. 9, the determination control apparatus 7A includes a determination section 71A, a signal output switching section 72A, a signal/information conversion section 73A, a control instruction section 74A, a communication section 75, and an antenna 76.

To the determination section 71A, the heart rate detected by the heart rate meter 150, the bending operation angle and the bending portion bending angle calculated by the calculation processing section 64A, the number of operations of the bending lever 17 within a certain time, a treatment instrument notifying signal outputted when the optical sensor 141 of the treatment instrument detector 140 detects the treatment instrument, and an energization notifying signal outputted from the high frequency power supply apparatus 132 for notifying of treatment with the electrosurgical knife 131 being performed as various medical action information are inputted. To the determination section 71A, the threshold of the patient's heart rate and the threshold of the frequency of the bending lever operation as medical action information thresholds are inputted. In this embodiment, the determination section 71A compares the patient's heart rate with the threshold thereof, compares the bending operation angle with the bending portion bending angle, and compares the frequency of the bending operation with the threshold thereof.

Then, the determination section 71A compares the threshold of the heart rate with the heart rate detected by the heart rate meter 150, and determines presence/absence of a load on the patient. Specifically, when the heart rate detected by the heart rate meter 150 is smaller than the threshold thereof, it is determined that a patient's condition is good ("1" in the drawing) as shown in FIG. 12, and the heart rate detected by the heart rate meter 150 is larger than the threshold thereof, it is determined that there is a load on the patient ("2" in the drawing).

The determination section 71A determines whether the bending operation angle matches the bending portion bending angle, and determines whether the distal end portion 11a or the like of the insertion portion is caught on a fold or the like in a tube cavity. Specifically, when the bending operation angle and the bending portion bending angle match, as shown in FIG. 12, it is determined that a bending operation is satisfactory and an endoscope operation is smoothly performed ("1" in the drawing), and when the bending operation angle is different from the bending portion bending angle, specifically, when the bending portion bending angle is smaller than the bending operation angle, it is determined that the distal end portion 11a is caught on a wall or it takes time to insert the insertion portion because of a sharp loop or the like ("2" in the drawing).

The determination section 71A compares the frequency of the bending operation with the threshold thereof, and determines whether the operator satisfactorily performs the bending operation without hesitation. Specifically, when the frequency of the bending operation is smaller than the threshold thereof, as shown in FIG. 12, it is determined that the bending operation is satisfactorily performed ("1" in the drawing), and when the frequency of the bending operation is larger than the threshold thereof, it is determined that it takes time to perform the bending operation ("2" in the drawing).

Next, the signal output switching section 72A will be described.

The signal output switching section 72A includes an upper doctor input section 72e and a lower doctor input section 72f as two input sections, an upper doctor switching section 72g and a lower doctor switching section 72h as two switching sections, a first output section 72i and a second output section 72k as two output sections, and an upper doctor waiting section 72m and a lower doctor waiting section 72n as two waiting sections.

To the upper doctor input section 72e, the control instruction signal outputted from the viewer 120 is inputted. To the lower doctor input section 72f, a bending operation signal outputted from the bending lever 17 and corresponding to the tilting operation of the bending lever 17a calculated by the calculation processing section 64A is inputted.

The upper doctor switching section 72g is a so-called switch that switches an output destination of the control instruction signal inputted to the upper doctor input section 72e to any of the first output section 72i, the second output section 72k, and the upper doctor waiting section 72m. The upper doctor switching section 72g has the output destination switched based on a switching signal outputted from the control instruction section 74A.

The lower doctor switching section 72h is a switch that switches an output destination of the bending operation signal inputted to the lower doctor input section 72f and corresponding to the tilting operation of the bending lever 17 to the second output section 72k or the lower doctor waiting section 72n. The lower doctor switching section 72h has the output destination switched based on a switching signal outputted from the control instruction section 74A.

The first output section 72i is connected to the signal/information conversion section 73A, and outputs a control instruction signal transmitted via the upper doctor switching section 72g to the first output section 72i, to the signal/information conversion section 73A. Meanwhile, the second output section 72k is connected to the endoscope control apparatus 6A. The second output section 72k outputs an operation instruction signal transmitted via the upper doctor switching section 72g to the second output section 72k or an operation instruction signal transmitted via the lower doctor switching section 72h to the second output section 72k, via the calculation processing section 64A to the motors 18 and 19 of the operation section 12B.

To the signal/information conversion section 73A, the video signal outputted from the endoscope control apparatus 6A, various medical action information inputted to the determination section 71A, and the control instruction signal outputted from the viewer 120 are inputted.

The bending direction and the bending operation angle of the bending operation angle, the bending direction and the bending angle of the bending portion bending angle, and the heart rate detected by the heart rate meter 150 inputted to the signal/information conversion section 73A are outputted in real time via the communication section 75 to the viewer 120. Thus, the medical instrument operation information display section 122a in the viewer 120 displays the direction and the angle, for example, by numerical values, such as R20 degrees (bend 20 degrees rightward) or R21 degrees (bend 21 degrees rightward). The patient information display section 122b in the viewer 120 displays the heart rate by numerals.

When the treatment instrument notifying signal outputted from the treatment instrument detector 140, and the energization notifying signal outputted from the high frequency treatment apparatus 130 are inputted to the signal/information conversion section 73A, a signal for notifying the viewer 120 of treatment being performed in real time via the communication section 75 is outputted. Thus, the treatment mode notifying section 122d in the viewer 120 enters, for example, a green light emitting state.

Meanwhile, when the treatment instrument detector 140 does not output the treatment instrument notifying signal to the signal/information conversion section 73A, the insertion/test mode notifying section 122e enters, for example, a green light emitting state.

When the treatment mode notifying section 122d is in the light emitting state, the insertion/test mode notifying section 122e enters a shutoff state. When the insertion/test mode notifying section 122e is in the light emitting state, the treatment mode notifying section 122d enters a shutoff state.

The control instruction section 74A determines a procedure situation of the lower doctor 104 based on each determination result of the determination section 71A, and a switching signal corresponding to the determination result is outputted to the signal output switching section 72A.

Specifically, the control instruction section 74A checks combinations of the determination results, and when all the determination results of the determination section 71A are "1" as shown in FIG. 12, the control instruction section 74A determines that the procedure situation is acquired (procedure situation "0" in the drawing). Meanwhile, when the all the determination results of the determination section 71A are "2", the control instruction section 74A determines that the procedure situation is unstable (procedure situation "2" in the drawing). When two of the determination results are "1" and one of the determination results is "2" as shown in FIG. 12, the control instruction section 74A determines that the procedure situation is satisfactory (procedure situation "1" in the drawing). When one of the determination results is "1" and two of the determination results are "2", the control instruction section 74A determines that the procedure situation is unstable.

When the control instruction section 74A determines that the procedure situation is acquired, the control instruction section 74A outputs a third switching signal to the signal output switching section 72A. Then, as shown in FIG. 13, the upper doctor switching section 72g is connected to the upper doctor waiting section 72m, and the lower doctor switching section 72h is connected to the second output section 72k. Thus, the control instruction signal transmitted from the viewer 120 operated by the upper doctor 103 is inputted to the upper doctor input section 72e, and then the input becomes invalid. Specifically, the control instruction section 74A prevents an unnecessary display on the screen 5a so that the lower doctor 104 can concentrate on the procedure. Thus, the bending operation signal corresponding to the tilting operation of the bending lever 17 of the lower doctor 104 is inputted to the lower doctor input section 72f, then inputted to the calculation processing section 64A of the endoscope control apparatus 6A, converted into the drive signals for driving the motors 18 and 19 and outputted to the motors 18 and 19.

When the control instruction section 74A determines that the procedure situation is satisfactory, the control instruction section 74A outputs a fourth switching signal to the signal output switching section 72A. Then, as shown in FIG. 14, the upper doctor switching section 72g is connected to the first output section 72i, and the lower doctor switching section 72h is connected to the second output section 72k.

Thus, the control instruction signal transmitted from the viewer 120 operated by the upper doctor 103 is inputted to the upper doctor input section 72e, and then outputted to the signal/information conversion section 73A. Meanwhile, the bending operation signal corresponding to the tilting operation of the bending lever 17 of the lower doctor 104 is inputted to the lower doctor input section 72f, then inputted to the calculation processing section 64A of the endoscope control apparatus 6A, and outputted to the motors 18 and 19 as described above.

Meanwhile, when the control instruction section 74A determines that the procedure situation is unstable, the control instruction section 74A outputs a fifth switching signal to the signal output switching section 72A. Then, as shown in FIG. 15, the upper doctor switching section 72g is connected to the second output section 72k, and the lower doctor switching section 72h is connected to the lower doctor waiting section 72n. Thus, the screen 5a displays a comment "Upper doctor performs operation from here" or the like to notify the lower doctor 104 of switching to the operation of the upper doctor 103. The bending portion 11b is bent based on the bending operation signal transmitted from the viewer 120 operated by the upper doctor 103 instead of the bending operation signal outputted from the bending lever 17 operated by the lower doctor 104.

The communication section 75 includes a radio antenna 76. The communication section 75 demodulates the control instruction signal from the viewer 120 received by the radio antenna 76 and outputs the signal to the upper doctor input section 72e. The communication section 75 modulates, for example, information for displaying the bending direction, information for displaying the bending operation angle, information for displaying the heart rate, or the like outputted from the signal/information conversion section 73A to the viewer 120, to a carrier wave of a predetermined frequency, and transmits the wave from the radio antenna 76.

A case will be described where a procedure for dissecting a polyp in the large intestine using the medical system 10A configured as described above.

In this embodiment, when the upper doctor 103 and the lower doctor 104 perform the procedure for dissecting the polyp in the large intestine, the lower doctor 104 performs the procedure in an operation room, and the upper doctor 103 carries the viewer 120 and is placed in a position remote from the operation room and communicable with the determination control apparatus 7A.

The lower doctor 104 checks a fitting state of the treatment instrument detector 140 to the treatment instrument insertion port 12a, checks a fitting position of the heart rate meter 150 to the patient 101, checks a position of the foot switch 133 of the high frequency treatment apparatus 130, and checks the type of the electrosurgical knife 131. After the checking, the lower doctor 104 starts the procedure. At this time, the upper doctor 103 understands the procedure of the lower doctor 104 using the viewer 120.

First, the lower doctor 104 starts an insertion procedure of the insertion portion 11E. In this procedure, the control instruction section 74A checks whether the treatment instrument notifying signal is outputted from the treatment instrument detector 140 to the determination section 71 as shown in Step S11 in FIG. 16. When the control instruction section 74A checks that the treatment instrument notifying signal is outputted, the control instruction section 74A determines that a treatment step S30 is performed. Meanwhile, when the treatment instrument notifying signal is not outputted, the control instruction section 74A determines that an insertion step S20 is performed. Then, the control instruction section 74A transmits information corresponding to the determination result from the communication section 75 to the viewer 120.

Thus, in the treatment step, the treatment mode notifying section 122d in the viewer 120 emits light, and in the insertion step, the insertion/test mode notifying section 122e emits light.

In the insertion step, the control instruction section 74A starts reviewing the determination result of the determination section 71A to determine whether the insertion procedure is satisfactory based on the determination result of the determination section 71A as shown in Step S21 in FIG. 17, and proceeds to Step S22.

The upper doctor 103 checks an endoscopic image on the touch panel 121 of the viewer 120, and various medical action information displayed on the medical action information display section 122, and understands the operation situation of the lower doctor 104.

In Step S22, the control instruction section 74A determines the procedure situation of the lower doctor 104 based on the determination result of the determination section 71A, and a switching signal corresponding to the determination result is outputted to the signal output switching section 72.

When the control instruction section 74A determines that the procedure is "unstable" despite immediately after the start of the insertion step, the control instruction section 74A proceeds to Step S23 and stops the insertion step. At this time, the control instruction section 74A displays a comment, for example, "Please check" on the screen 5a via the signal/information conversion section 73A and encourages checking.

Meanwhile, when the control instruction section 74A determines that the procedure is "acquired", the control instruction section 74A proceeds to Step S24, and outputs the third switching signal to the signal output switching section 72A and proceeds to Step S25. In Step S24, the third switching signal is outputted from the control instruction section 74A to the signal output switching section 72A, and thus the lower doctor 104 continues the procedure. At this time, as described above, the upper doctor switching section 72g is switched to the upper doctor waiting section 72m, and thus the signal from the upper doctor is not displayed on the screen 5a visually identified by the lower doctor 104.

When the control instruction section 74A determines in Step S22 that the procedure is "satisfactory", the control instruction section 74A proceeds to Step S26, and outputs the fourth switching signal to the signal output switching section 72A and proceeds to Step S25. In Step S26, the fourth switching signal is outputted from the control instruction section 74A to the signal output switching section 72A. Thus, when the control instruction signal transmitted from the viewer 120 of the upper doctor 103 is inputted to the upper doctor input section 72e, the screen 5a displays a comment such as "Bend rightward" for an instruction of a bending direction, or an arrow indicating the bending direction. At this time, the lower doctor 104 checks the operation instruction from the upper doctor 103 displayed on the screen 5a and continues the procedure.

In Step S25, while the control instruction section 74A determines that the procedure is "acquired", the third switching signal is outputted to the signal output switching section 72A. Thus, the lower doctor 104 can introduce the insertion portion 11E into a target area by him/herself without receiving the operation instruction from the upper doctor 103. When the insertion portion 11E reaches the target area, the control instruction section 74A finishes the insertion procedure and proceeds to a treatment step. Specifically, the lower doctor 104 performs endoscopic observation of the polyp.

In Step S25, while the control instruction section 74A determines that the procedure is "satisfactory", the fourth switching signal is outputted to the signal output switching section 72A. Thus, the screen 5a displays an endoscopic image, and also an operation instruction from the upper doctor 103 when the control instruction signal is inputted to the upper doctor input section 72e. When the insertion portion 11E reaches the target area, the control instruction section 74A finishes the insertion procedure and proceeds to the treatment step as described above.

Meanwhile, in Step S25, when the control instruction section 74A determines that the procedure is "unstable", the control instruction section 74A proceeds to Step S27. In Step S27, the control instruction section 74A notifies of stop of the insertion procedure of the lower doctor 104, and outputs the fifth switching signal to the signal output switching section 72A and proceeds to Step S28. At this time, the screen 5a displays a comment, for example "Upper doctor performs operation from here", and the bending operation signal outputted from the bending lever 17 operated by the lower doctor 104 becomes invalid.

The fifth switching signal is outputted to the signal output switching section 72A, and thus the control instruction signal transmitted from the viewer 120 operated by the upper doctor 103 is inputted from the upper doctor input section 72e to the endoscope control apparatus 6A as a bending operation signal, and converted into drive control signals for driving the motors 18 and 19. Thus, the drive forces of the motors 18 and 19 cause the bending wire to be pulled/slackened and the bending portion 11b is bent according to the instruction from the upper doctor 103, thereby resolving the unstable situation.

When the operation of the upper doctor 103 causes changes such that the number of operations of the bending lever 17 by the lower doctor 104 is reduced, the heart rate of the patient 101 is reduced, or the bending operation angle matches the bending portion bending angle, and the control instruction section 74A again determines that the procedure is "satisfactory", the control instruction section 74A proceeds to Step S29.

In Step S29, the control instruction section 74A checks whether the procedure of the lower doctor 104 is restarted. Specifically, the control instruction section 74A causes the touch panel 121 to display a comment "Is procedure of lower doctor restarted?", and proceeds to Step S26 and outputs the fourth switching signal to the signal output switching section 72A.

When the upper doctor 103 selects "Restart" from the operation instruction list displayed on the touch panel 121, the screen 5a displays a comment "Procedure of lower doctor is restarted". Thus, the procedure of the lower doctor is restarted.

Meanwhile, when the upper doctor 103 determines that it is difficult to continue the procedure of the lower doctor 104, the upper doctor 103 selects "Finish" from the operation instruction list displayed on the touch panel 121. Then, the screen 5a displays a comment "Change to another doctor". Thus, another doctor replaces the lower doctor 104 and restarts the procedure. When there is no another doctor, the lower doctor 103 removes the insertion portion 11E.

Next, the treatment step will be described.

First, after the lower doctor 104 finishes the endoscopic observation of the polyp, the lower doctor 104 inserts the electrosurgical knife 131 via the treatment instrument detector 140 through the treatment instrument insertion channel 11d.

When the electrosurgical knife 131 is inserted through the treatment instrument insertion channel 11d, the control instruction section 74A checks that the treatment instrument notifying signal is outputted as shown in Step S11 in FIG. 16, and determines that the treatment Step S30 is performed. The control instruction section 74A transmits information corresponding to the determination result from the communication section 75 to the viewer 120. Specifically, the treatment mode notifying section 122d is caused to emit light instead of the insertion/test mode notifying section 122e in the viewer 120 being caused to emit light.

In the treatment step, the control instruction section 74A first checks whether the energization notifying signal is outputted from the high frequency power supply apparatus 132 of the high frequency treatment apparatus 130 to the determination section 71 as shown in Step S31 in FIG. 18. When the energization notifying signal is not outputted, the control instruction section 74A determines that the treatment is not performed and proceeds to Step S32. Meanwhile, when the energization notifying signal is outputted, the control instruction section 74A proceeds to Step S33 and stops the treatment step. At this time, the control instruction section 74A outputs a control signal for turning off the high frequency power supply apparatus 132, and displays a comment, for example "High frequency power supply apparatus was turned off. Do you continue procedure?" on the screen 5a via the signal/information conversion section 73A. Thus, even immediately after the start of the treatment step, that is, immediately after the start of the insertion of the electrosurgical knife 131 into the treatment instrument insertion channel 11d, defects caused by an abnormality of an "energization state" can be prevented.

In Step S32, the control instruction section 74A outputs the fourth switching signal to the signal output switching section 72A and proceeds to Step S34. In Step S32, when the fourth switching signal is outputted from the control instruction section 74A to the signal output switching section 72A and thus the control instruction signal is transmitted from the upper doctor 103, the instruction is displayed on the screen 5a. Specifically, the upper doctor 103 can display, on the screen 5a, dissection line information for dissecting, for example, a polyp or some instructions written on the touch panel 121 of the viewer 120 for an instruction.

In Step S34, the control instruction section 74A determines whether the determination result of the determination section 71A is "acquired", "satisfactory", or "unstable". When the control instruction section 74A detects that the result is unstable, the control instruction section 74A proceeds to Step S35, and when other results are determined, the control instruction section 74A proceeds to Step S36. In Step S35, the control instruction section 74A displays, on the screen 5a, a comment, for example "It was determined that procedure was unstable. Does something happen? Can you restart?". When the control instruction section 74A checks a signal from the lower doctor 104 that the procedure can be restarted, the control instruction section 74A proceeds to Step S36. Meanwhile, when the control instruction section 74A checks a signal from the lower doctor 104 that the procedure cannot be restarted, the control instruction section 74A finishes the treatment. Information that the procedure can or cannot be restarted is provided, for example, by a response apparatus 160 provided in the operation section 12B and having switches 161 and 162.

In Step S36, when the control instruction section 74A checks an instruction to start dissection from the upper doctor 103, the control instruction section 74A proceeds to Step S37. Meanwhile, when the control instruction section 74A checks an instruction to stop the procedure from the upper doctor 103, the control instruction section 74A finishes the treatment. When the instruction from the upper doctor 103 is not inputted, the control instruction section 74A returns to Step S32 and waits for the instruction from the upper doctor 103.

The instruction to start or stop the dissection is given by the high frequency switch 123 provided in the viewer 120. Specifically, the upper doctor 103 operates the ON button 123a for a start instruction, and operates the OFF button 123b for a stop instruction.

In Step S37, the control instruction section 74A checks whether the energization notifying signal is outputted from the high frequency power supply apparatus 132 of the high frequency treatment apparatus 130 to the determination section 71. When the energization notifying signal is not outputted, the control instruction section 74A determines that the treatment is not performed and proceeds to Step S32. Meanwhile, when the energization notifying signal is outputted, the control instruction section 74A proceeds to Step S38.

In Step S38, the control instruction section 74A outputs the third switching signal to the signal output switching section 72A and moves to Step S39. The third switching signal is outputted from the control instruction section 74A to the signal output switching section 72A in Step S38, and thus the lower doctor 104 performs dissection. At this time, even if the upper doctor 103 operates the viewer 120 and transmits some control instruction signal, the signal from the upper doctor is not displayed on the screen 5a visually identified by the lower doctor 104.

In Step S39, the control instruction section 74A determines whether the procedure is "acquired", "satisfactory", or "unstable" based on the determination result of the determination section 71A. When the control instruction section 74A determines that the procedure is "unstable" based on the determination result of the determination section 71A, the control instruction section 74A outputs a control signal for turning off the high frequency power supply apparatus 132, and proceeds to Step S35. At this time, the control instruction section 74A displays a comment, for example, "High frequency power supply apparatus was turned off. Do you continue procedure?" on the screen 5a via the signal/information conversion section 73A, and checks whether the lower doctor 104 continues the procedure.

When the control instruction section 74A checks a signal of continuation from the lower doctor 104, the control instruction section 74A proceeds to Step S36 as described above. Meanwhile, when the control instruction section 74A checks a signal of stop from the lower doctor 104, the control instruction section 74A finishes the treatment, and displays a comment "Change doctor" on the screen 5a. Then, another doctor replaces the lower doctor 104 and restarts the dissection.

The signal of continuation or stop is provided by the switches 161 and 162 of the response apparatus 160. When the control instruction section 74A checks the instruction to stop from the upper doctor 103 in Step S36, the control instruction section 74A displays a comment "Change doctor" on the screen 5a. Then, another doctor replaces the lower doctor 104 and restarts the dissection.

Meanwhile, when the control instruction section 74A determines that the procedure is "acquired" or "satisfactory" based on the determination result of the determination section 71A, the control instruction section 74A proceeds to Step S37. The lower doctor 104 operates the OFF switch 133b of the foot switch 133 to display the instruction from the upper doctor 103 on the screen 5a. Thus, the lower doctor 104 checks the instruction and restarts the dissection.

When the lower doctor 104 outputs a signal of finish of the dissection in Step S39, the control instruction section 74A proceeds to Step S40.

In Step S40, the control instruction section 74A outputs the fourth switching signal to the signal output switching section 72A, displays a comment "Do you finish procedure of dissection?" on the screen 5a, and enters a waiting state to wait for an instruction from the upper doctor 103.

When the instruction of "continuation" from the upper doctor 103 is checked, the control instruction section 74A returns to Step S32. The lower doctor 104 restarts the procedure according to an instruction "Move to dissection of next polyp" or the like from the upper doctor 103.

Meanwhile, when the control instruction section 74A checks an instruction "Finish dissection" from the upper doctor 103, the control instruction section 74A displays a comment "Finish" on the screen 5a. Thus, the dissection by the lower doctor 104 is finished. Then, the lower doctor 104 removes the insertion portion 11E from the body of the patient 101.

The instructions to finish or continue the dissection is given by the high frequency switch 123 provided in the viewer 120. Specifically, the upper doctor 103 operates the ON button 123a for a restart instruction, and operates the OFF button 123b for a finish instruction.

As such, the endoscope system including the medical instrument that can be operated by the upper doctor and the lower doctor includes the viewer and the determination control apparatus. Thus, while the determination control apparatus determines that the procedure of the lower doctor is satisfactory, the upper doctor can make inputs from the touch panel of the viewer to give the operation instruction to the lower doctor.

When the determination control apparatus determines that the procedure is unstable, the output of the lower doctor is made invalid, and the control instruction signal outputted from the upper doctor controller operated by the upper doctor can operate the medical instrument. This eliminates the need for troublesome work such as a shift of a medical apparatus between the lower doctor and the upper doctor, prevents overlaps of input operations, and reliably resolves the unstable situation.

Further, the information inputted from the touch panel of the viewer is made invalid while the determination control apparatus determines that the procedure of the lower doctor is acquired, and thus the lower doctor can concentrate on the procedure.

Other operations and effects are the same as in the first embodiment.

The present invention is not limited to the above-described embodiments, but may be modified in various manners without departing from the gist of the invention.

What is claimed is:

1. A medical system comprising:
 a first operation apparatus used when a first doctor operates a medical instrument;
 a second operation apparatus that outputs a control instruction signal for controlling a motion of the medical instrument, and is operated by a second doctor;
 at least one medical action information detection section that detects medical action information based on the motion of the medical instrument when the first doctor operates the medical instrument using the first operation apparatus;
 a storage apparatus that stores a threshold of an insertion portion grasping force set by the second doctor based on grip strength of the first doctor as reference information for comparing with the medical action information detected by the medical action information detection section and a threshold of an anal contraction force set by the second doctor in view of a technical level of the first doctor as the reference information;
 a switching signal generation apparatus that is connected to the second operation apparatus, and switches an output destination of the control instruction signal based on the medical action information detected by the medical action information detection section and the reference information stored in the storage apparatus; and
 a medical instrument control apparatus that controls the medical instrument according to the control instruction signal of the second operation apparatus outputted from the switching signal generation apparatus.

2. The medical system according to claim 1, further comprising an information display section that displays the medical action information of the first doctor to be observed by the second doctor when the medical instrument is operated by the first doctor.

3. The medical system according to claim 1, wherein
 the medical action information detection section includes a living body information detection section that detects living body information of a patient, and
 the switching signal generation apparatus generates the switching signal based on a determination result obtained by comparing the living body information of the patient with the reference information set by the second doctor.

4. The medical system according to claim 3, wherein
the medical action information detection section further includes an operation information detection section that detects operation input information of the first operation apparatus by the first doctor, and
the switching signal generation apparatus generates the switching signal based on a determination result obtained by comparing the living body information of the patient and the operation input information with the reference information set by the second doctor.

5. The medical system according to claim 4, wherein
the medical action information detection section further includes a driving state detection section that detects a parameter on a driving state of the medical instrument, and
the switching signal generation apparatus generates the switching signal based on a determination result obtained by comparing the living body information and the operation input information with the reference information set by the second doctor, and a determination result obtained by comparing the parameter with an operation result of the first doctor.

6. The medical system according to claim 1, wherein
the medical action information detection section comprises a living body information detection section that detects living body information of a patient, an operation information detection section that detects operation input information of the first operation apparatus by the first doctor, and a driving state detection section that detects a parameter on a driving state of the medical instrument, and
the switching signal generation apparatus generates the switching signal based on a determination result obtained by comparing the living body information of the patient with the reference information set by the second doctor, a determination result obtained by comparing the operation input information with the reference information set by the second doctor, and a determination result obtained by comparing the parameter with an operation result of the first doctor.

7. The medical system according to claim 6, further comprising an information display section that displays the medical action information of the first doctor to be observed by the second doctor when the medical instrument is operated by the first doctor,
wherein the information display section is capable of displaying determination result obtained by comparing the living body information of the patient with the reference information set by the second doctor, the determination result obtained by comparing the operation input information with the reference information set by the second doctor and the determination result obtained by comparing the parameter with the operation result of the first doctor, and further the living body information, the operation input information and the parameter on the information display section.

8. A medical system comprising:
a first operation apparatus used when a first doctor operates a medical instrument;
a second operation apparatus that is operated by a second doctor, and outputs a control instruction signal including an operation instruction to the first doctor, and a control signal for controlling a motion of the medical instrument;
at least one medical action information detection section that detects medical action information based on the motion of the medical instrument when the first doctor operates the medical instrument using the first operation apparatus;
a storage apparatus that stores threshold information for determining a procedure situation of the first doctor from the medical action information outputted from the medical action information detection section; and
a determination control apparatus including
a determination section that compares the medical action information with the threshold information stored in the storage apparatus, and
a switching section that outputs the control instruction signal outputted from the second operation apparatus as an operation instruction to the first doctor or as the control signal for controlling the motion of the medical instrument based on a determination result of the determination section.

* * * * *